United States Patent
Caras et al.

(10) Patent No.: US 7,067,484 B1
(45) Date of Patent: *Jun. 27, 2006

(54) AL-1 NEUROTROPHIC FACTOR TREATMENTS

(75) Inventors: Ingrid W. Caras, San Francisco, CA (US); John W. Winslow, El Granada, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/914,319

(22) Filed: Aug. 18, 1997

Related U.S. Application Data

(63) Continuation of application No. 08/330,128, filed on Oct. 27, 1994, now abandoned.

(51) Int. Cl.
*A61K 38/18* (2006.01)

(52) U.S. Cl. ........................................... 514/12

(58) Field of Classification Search ................ 435/368, 435/375, 7.1; 530/350; 514/12; 424/134.1, 424/135.1, 377
See application file for complete search history.

(56) References Cited

U.S. PATENT DOCUMENTS 6,280,732 B1 * 8/2001 Caras et al. .............. 424/178.1

FOREIGN PATENT DOCUMENTS

| EP | 597.503 A2 | 5/1994 |
| WO | WO 90/02798 | 3/1990 |
| WO | WO 91/06667 | 5/1991 |
| WO | WO 94/11384 | 5/1994 |
| WO | WO 95/02421 | 2/1995 |
| WO | WO 95/27060 | 10/1995 |
| WO | WO 96/17925 | 6/1996 |

OTHER PUBLICATIONS

Talmadge et al. Advanced Drug Delivery Reviews 10:247. 299, 1993.*
Jackowski British J Neurosurgery 9:303-317, 1995.*
Bartley et al., "B61 is a ligand for the ECK receptor protein-tyrosine kinase" *Nature* 368:558-560 (Apr. 7, 1994).
Beckmann et al., "Molecular characterization of a family of ligands for eph-related tyrosine kinase receptors" *EMBO Journal* 13(16):3757-3762 (1994).
Berkemeier et al., "Neurotrophin-5: A Novel Neurotrophic Factor That Activates trk and trkB" *Neuron* 7:857-866 (Nov. 1991).
Byrn et al., "Biological properties of a CD4 immunoadhesin" *Nature* 344:667-670 (Apr. 12, 1990).
Capon et al., "Designing CD4 immunoadhesins for AIDS therapy" *Nature* 337:525-531 (Feb. 9, 1989).

Gilardi-Hebenstreit et al., "An Eph-related receptor protein tyrosine kinase gene segmentally expressed in the developing mouse hindbrain" *Oncogene* 7:2499-2506 (1992).
Hefti, Franz, "Nerve Growth Factor Promotes Survival of Septal Cholinergic Neurons After Fimbrial Transections" *J. of Neuroscience* 6(8):2155-2162 (Aug. 1986).
Heumann, Rolf, "Regulation of the Synthesis of Nerve Growth Factor" *J. Exp. Biol.* 132:133-150 (1987).
Kaisho et al. *FEBS Letters* 266(1,2):187-191 (Jun. 1990).
Lai et al., "An Extended Family of Protein-Tyrosine Kinase Genes Differentially Expressed in the Vertebrate Nervous System" *Neuron* 6:691-704 (May 1991).
Leibrock et al., "Molecular cloning and expression of brain-derived neurotrophic factor" *Nature* 341:149-152 (Sep. 14, 1999).
Maisonpierre et al., "Ehk-1 and Ehk-2: two novel members of the Eph receptor-like tyrosine kinase family with distinctive structures and neuronal expression" *Oncogene* 8:3277-3288 (1993).
Maisonpierre et al., "Neurotrophin-3: A Neurotrophic Factor Related to NGF and BDNF" *Science* 247:1446-1451 (Mar. 23, 1990).
Rosenthal et al., "Primary Structure and Biological Activity of a Novel Human Neurotrophic Factor" *Neutron* 4:767-773 (May 1990).
Thoenen et al., "Physiology of Nerve Growth Factor" *Physiological Reviews* 60(4):1284-1335 (Oct. 1980).
Tuzi et al., "eph, the largest known family of putative growth factor receptors" *Br. J. Cancer* 69:417-421 (1994).
Zhou et al., "Isolation and Characterization of Bsk, a Growth Factor Receptor-Like Tyrosine Kinase Associated With the Limbic System" *J. of Neur. Res.* 37:129-143 (1994).
Friden, P.M., "Receptor-mediated transport of therapeutics across the blood-brain barrier", Neurosurgery 35(2):294-298, (Aug. 1994).
Pandey et al., "Role of B61, the Ligand for the EckREceptor Tyrosine Kinase, in TNF-α-Induced Angiogenesis", Science 268:567-569 (1995).
Camarata et al., "Sustained Release of Nerve Growth Factor from Biodegradable Polymer Microspheres" *Neurosurgery* 30(3):313-319 (1992).
Canal, "Degenerative Disorders" *Guidelines for Drug Trials in Memory Disorders* 39:19-24 (1993).

(Continued)

*Primary Examiner*—Robert C. Hayes
(74) *Attorney, Agent, or Firm*—Ginger R. Dreger; Atulya R. Agarwal; Heller Ehrman LLP

(57) ABSTRACT

The present invention provides nucleic acids encoding AL-1 protein, as well as AL-1 protein produced by recombinant DNA methods. Such AL-1 protein is useful in preparing antibodies and in diagnosing and treating various neuronal disorders.

4 Claims, 5 Drawing Sheets

OTHER PUBLICATIONS

Cerretti et al., "The Gene Encoding LERK-7 (EPGL&, EpI7), a Ligand for the Eph-related Tyrosine Kinases, Maps to Human Chromosome 5 at Band q21 and to Mouse Chromosome 17" *Genomics* 35:376-379 (1996).

Cheng et al., "Identification and Cloning of ELF-1, a Developmentally Expressed Ligand for the Hek4 and Sek Receptor Tyrosine Kinases" *Cell* 79:157-168 (Oct. 7, 1994).

Davis et al., "Ligands for EPH-Related Receptor Tyrosine Kinases That Require Membrane Attachment or Clustering for Activity" *Science* 266:816-819 (Nov. 4, 1994).

de Leon et al., "In Vivo Structural Studies of the Hippocampus in Normal Aging and in Incipient Alzheimer's Disease" *Annals of the New York Academy of Sciences* 777:1-13 (1996).

Drescher et al., "In Vitro Guidance of Retinal Ganglion Cell Axons by RAGS, a 25 kDa Tectal Protein Related to Ligands for Eph Receptor Tyrosine Kinases" *Cell* 82:359-370 (1995).

Fox et al., "Atrophy of the Hippocampal Formation in Early Familial Alzheimer's Disease: A Longitudinal MRI Study of at-Risk Members of a Family With an Amyloid Precursor Protein 717 Val-Gly Mutation" *Annals of the New York Academy of Sciences* 777:226-232 (1995).

Hefti, F., "Neurotrophic Factor Therapy for Nervous System Degenerative Diseases" *Journal of Neurobiology* 25(11):1418-1435 (1994).

Mutson et al., "Intrastriatal and Intraventricular Infusion of Brain-Derived Neurotrophic Factor in the Cynomologous Monkey: Distribution, Retrograde Transport and Co-Localization with Substantia Nigra Dopamine-Containing Neurons" *Neuroscience* 71(1):179-191 (1996).

Ringold et al. "Co-expression and Amplification of Dihydrofolate Reductase cDNA and the *Escherichia coli* XGPRT Gene in Chinese Hamster Ovary Cells" *Journal of Molecular & Applied Genetics* 1(3):165-175 (1981).

Winslow et al., "Cloning of AL-1, a Ligand for an Eph-Related Tyrosine Kinase Receptor Involved in Axon Bundle Formation" *Neuron* 14:973-981 (May 1995).

Barinaga, Marcia, "Receptors Find Work As Guides", Science, vol. 269, pp. 1668-1670, Sep. 22, 1995.

Hefti et al., "Chronic Administration of Nerve Growth Factor and Other Neurotrophic Factors to the Brain", Neurobiology of Aging, vol. 9, pp. 689-690, 1998.

Olson, Lars, "NGF and the Treatment of Alzheimer's Disease", Experimental Neurology, vol. 124, pp. 5-15, 1993.

Olson, Lars, "Intraputaminal Infusion of Nerve Growth Factor to Support Adrenal Medullary Autografts in Parkinson's Disease- One Year Follow-up of First Clinical Trial", Arch. Neurol., vol. 48, pp. 373-381, Apr. 1994.

Tomlinson, B.E., "Ageing and the Dementias", Greenfield's Neuropathology, J. Hume Adams, Lee W. Duchen, Fifth edition, New York: Oxford University Press, Chapter 20, pp. 1284-1410, 1992.

\* cited by examiner

FIG.1A

```
1237 AAA AAA TGT CCT TCT GTA GTT AGA CAT TTG GCT GTT TTC CCT GAC ACG ATC ACT GGA GCA GAT TCT CCA GAG TTG CTA GAG
 233 Lys Lys Cys Pro Ser Val Val Arg His Leu Ala Val Phe Pro Asp Thr Ile Thr Gly Ala Asp Ser Ser Gln Leu Leu Glu

1318 GTG TCA GGC TCC TGC GTC GTG AAC CAT TCT GTG ACA GAC GAT CCT CCC AAA ATG GCA GAT TGC CAT TGC GAA GGG GAG TGG CTG GTT
 260 Val Ser Gly Ser Cys Val Val Asn His Ser Val Thr Asp Asp Pro Pro Lys Met Ala Asp Cys His Cys Glu Gly Glu Trp Leu Val

1399 CCC ATC GGG AAA TGC ATG AAG TGC GGA TAT GCC AAG AAA AAT GGT ACC TGT CAA GTG TGC AGA CCT GGG TTC TTC AAA
 287 Pro Ile Gly Lys Cys Met Lys Cys Gly Tyr Ala Lys Lys Asn Gly Thr Cys Gln Val Cys Arg Pro Gly Phe Phe Lys

1480 GCC TCT CCT CAC AGC CAG ACC TGC AGC AAA TGT CCA CCT CAC TAC ACC CAT GAG GAA GCT TCC ACC TGT GTC TGT
 314 Ala Ser Pro His Ser Gln Thr Cys Ser Lys Cys Pro Pro His Tyr Thr His Glu Glu Ala Ser Thr Cys Val Cys

1561 GAA AAG GAT TAT TTC AGG AGG GAA TCT GAT CCG CCC ACA ATG GCA TGC ACA ACT CCT TCT CCA GTC ACC AAC GTG AAG AAG
 341 Glu Lys Asp Tyr Phe Arg Arg Glu Ser Asp Pro Pro Thr Met Ala Cys Thr Thr Pro Ser Pro Val Thr Asn Val Lys Lys

1642 GGG AAG ATC GCA AAG AGC ATT TCT TTG TCT GCA GTT CAA TCT AAT GAT CAA AGC CAG ATT CCC AAT GGG ATC ATC CTG GAG TAC GGA GTC ATC
 368 Gly Lys Ile Ala Lys Ser Ile Ser Leu Ser Ala Val Gln Ser Asn Asp Gln Ser Gln Ile Pro Asn Gly Ile Ile Leu Glu Tyr Gly Val Ile

1723 AAG TAC TTT GAA GAG AAG GAC CAA CAG AGC TAC ACA ATT ATC AAG TCT AAA GAG ACC ACT ATT ACG GCA GAG GGC CTG AAA
 395 Lys Tyr Phe Glu Glu Lys Asp Gln Gln Ser Tyr Thr Ile Ile Lys Ser Lys Glu Thr Thr Ile Thr Ala Glu Gly Leu Lys

1804 CCT GCG TCT GTG TAT GTC TTC TTC CAA ATT CGA GCA GCA CGT ACA GCA GGC GTC TTC AGT CGA CGG TTT GAG TTT GAA
 422 Pro Ala Ser Val Tyr Val Phe Phe Gln Ile Arg Ala Ala Arg Thr Ala Gly Val Phe Ser Arg Arg Phe Glu Phe Glu

1885 ACC ACA CCA GTC TCA GTT GCA GCA TCT AAT GAT CAA AGC CAG ATT CCC ATC GCG GTG TCA GTG ACG TCA GCT TCT CCC CTG TGC GCT
 449 Thr Thr Pro Val Ser Val Ala Ala Ser Asn Asp Gln Ser Gln Ile Pro Ile Ala Val Ser Val Thr Val Gly Val Ile Leu Cys Ala

1966 TTG TTG GCA GTG ATG ATC GGC TTC CTC TTT TGC TGG AGG GCT TCT CGT GCA GAA GAG ATG CAC TTT CAT
 476 Leu Leu Ala Val Met Ile Gly Phe Leu Phe Cys Trp Arg Ala Ser Arg Ala Glu Glu Met His Phe His

2047 GTT GCC CAT CCA AGC CTA ATA ATC TGG CGG TGT TAC GGG TGT AAA GCA GAT CCA AAG CAC CAC GTT CAA GCC GTT CAT
 503 Val Ala His Pro Ser Leu Ile Ile Trp Arg Cys Tyr Gly Cys Lys Ala Asp Pro Lys His His Val Gln Ala Val His

2128 AAC GGG CAC ATT AAA CTG CCA GGA GTA AGA ACG TAC ATT GAT CCA ACC TAC ATT GAT CCC ACT CAA GCC GTT CAT GAA
 530 Asn Gly His Ile Lys Leu Pro Gly Val Arg Thr Tyr Ile Asp Pro Thr Tyr Ile Asp Pro Thr Gln Ala Val His Glu

2209 TTT GCC AAG GAG ATC GAG GCC TCA TGC ATC ACC ATT GAG AGA GTT ATT GGA GCA GGT GAA TTT GGT GAA GTT TGT AGT GGA
 557 Phe Ala Lys Glu Ile Glu Ala Ser Cys Ile Thr Ile Glu Arg Val Ile Gly Ala Gly Glu Phe Gly Glu Val Cys Ser Gly
```

FIG. 1B

```
2290 CGT TTG AAA CTA CCC GGA AAA AGA GAA TTG CCT GTG GCT ATC AAA ACT CTT AAA GTA GGC TAC ACT GAA AAG CAG CGC AGA
 584 Arg Leu Lys Leu Pro Gly Lys Arg Glu Leu Pro Val Ala Ile Lys Thr Leu Lys Val Gly Tyr Thr Glu Lys Gln Arg Arg

2371 GAT TTT CTG AGT GAA GCG AGT ATC ATG GGG CAG TTT GAT CAT CCA AAC ATC ATC CAT CTA GAA GGC GTT GTG ACT AAA AGT
 611 Asp Phe Leu Ser Glu Ala Ser Ile Met Gly Gln Phe Asp His Pro Asn Ile Ile His Leu Glu Gly Val Val Thr Lys Ser

2452 AAA CCT GTG ATG GTG ATA ACA GAG TAC ATG GAG AAT GGC TCC TTA GAC ACA TTT TTA AAG AAA GAT GGC CAG TTC ACT
 638 Lys Pro Val Met Val Ile Thr Glu Tyr Met Glu Asn Gly Ser Leu Asp Thr Phe Leu Lys Lys Asn Asp Gly Gln Phe Thr

2533 GTG ATT CAG CTT GTT GGC ATG CTG AGA GGC ATC GCT GCA GGA ATG AAG TAC CTT TCT GAC GTG CAC GTG TAC GTG CAC AGA GAC
 665 Val Ile Gln Leu Val Gly Met Leu Arg Gly Ile Ala Ala Gly Met Lys Tyr Leu Ser Asp Met Gly Tyr Val His Arg Asp

2614 CTT GCT GCT AGA AAC ATC TTA TTA ATC AAC AGT AAT CTT GTG TGC AAA GTG TCT GAC TTT GGA CTT TCC AGG GTG GAA GAT
 692 Leu Ala Ala Arg Asn Ile Leu Leu Ile Asn Ser Asn Leu Val Cys Lys Val Ser Asp Phe Gly Leu Ser Arg Val Leu Glu Asp

2695 GAT CCT GAG GCA GCC TAT ACC ACA AGG GGA AAA ATT CCA ATC AGG TGG ACT GCT CCA GAA GCA ATA GCT TTT CGA AAG
 719 Asp Pro Glu Ala Ala Tyr Thr Thr Arg Gly Lys Ile Pro Ile Arg Trp Thr Ala Pro Glu Ala Ile Ala Phe Arg Lys

2776 TTT ACC TCT GCC AGT GAT GTC TGG AGC TAT GGA GTT GTG TCC TAT GAG ATA CCC ATG GAT TGT CCT GCT GCC CTC TAT
 746 Phe Thr Ser Ala Ser Asp Val Trp Ser Tyr Gly Val Val Ser Tyr Glu Ile Leu Arg Pro Tyr Trp Glu

2857 ATG ACC AAT CAG GAT GTG ATC GTG GAA GTG GTA GGC TAC CGC CTG CCA AGC CCC ATG GAT TGT CCT GCT GCC CTC TAT
 773 Met Thr Asn Gln Asp Val Ile Val Glu Val Val Gly Tyr Arg Leu Pro Ser Pro Met Asp Cys Pro Ala Leu Tyr

2938 CAA TTA ATG CTG GAT TGC TGG CAG TGG CAG CCC AAG CCC AAG CCC AAG CCC AAC AGC AGG AAC AGC AGG GTA TTT GAT GAC ATA GTC AAC ATG CTG GAT AAG CTG
 800 Gln Leu Met Leu Asp Cys Trp Gln Trp Gln Pro Lys Asp Pro Lys Pro Lys Pro Asn Ser Arg Asn Ser Arg Val Phe Asp Asp Ile Val Asn Met Leu Asp Lys Leu

3019 ATA CGA AAC CCA AGT AGT TTG CAA CAA CTG CTG AGG ACA GTA AGG AGG GTA TCA AGC AGG GTA TCA AGC AGG GCG TCA AGC AGG GTA TTG GCA GAA CAT GGA TCT TTG
 827 Ile Arg Asn Pro Ser Ser Leu Gln Gln Leu Leu Arg Thr Val Ser Arg Val Ser Arg Ala Ser Arg Val Leu Leu Ala Glu His Gly Ser Leu

3100 GGG TCT GGG GCC TAC TCA AGA AGT GAT GCT GTT GCA ATC GCT CAA TTA CTA TGC CCT CAG CTG GAG GAT ACA GAG ATT TTC ATG GAA AAT
 854 Gly Ser Gly Ala Tyr Arg Ser Val Ala Gln Ala Val Ala Gln Val Leu Thr Thr Thr Thr Leu Thr Ala Glu Ile Phe Met Glu Asn

3181 GGA TAC AGT TCA ATG GAC GAT ATG AAA GAC GTT GTT GAG AGA GTG AGT AGT CTT GAG GTG CAC CAG
 881 Gly Tyr Ser Ser Met Asp Ala Val Ala Gln Val Leu Thr Ala Gln Val Leu Gly Val Val Gly Val Thr Leu Val Gly Val Gly Val Gly Val His Gln
```

FIG. IC

```
3262 AAG AAG ATC ATG ATG AAC AGC CTT CAA GAG ATG AAG GTG CAG CTG GTA AAC GGG ATG GTG CCA GTG TGA    CCC GCACACGGGT
 908 Lys Lys Ile Met Met Asn Ser Leu Gln Glu Met Lys Val Gln Leu Val Asn Gly Met Val Pro Val OP*

3341 CACTTCTCCA AGTGAACAAC TCTGCACTTT GTAAACAGCC CTAAGATTTA TTTTAACAGA GAAAGGGAAA TGGGTGGTTC CTAAACCTTT GAAGGCACTT

3441 GTCTCATCCT TTGACTTATA ATCAACATTT TCCAGATCTT CTTCTTAATG TCTTCGTTTT TTTCACTATG TAAATGTAAC CTGCGAAGAG

3541 AGCTAACATG AGAAACAACA TCCTATAAAA ACATAGTAAC TCCACTGCA GCCCCTTTCA AAACTACCAG GGATCGACTT GAAAGGAAAA

3641 GTTTTAAAGC CATGTGTGGG CAAAGAAACG CTGCATTTTA CTTCGAGTTT TATTTGTCTG CATAAGTGTA TTGGAGAGCA ATATGATTAG

3741 ATTATTTCTT AAATACAGTT TGTAATTTAA AATGGAATTA CATGTTATAA GTTATAGAAA ATAGTTTACA GACATGTTGC CCGGTCAAGG AAAAGTTCAG

3841 CACAGGGTGT ATATTTATTT TTCTGTGTTA TATAATTTAC ACTTCTAGAG AGTATTAGGC AATGAATGTG TATAGACTGT ATAGTTTGCA

3941 ATATACCGAG GAATGGACTT AAATTGGAAA TGTATGTATA TGTGCGTATG TGTGTGTGTG TTTGAAATAT TAGATGGTAT TGTTCTGCTT

4041 GCCTTTTGTA TAGGGTTTTA ATTTTGGCCT CATACAGCAA AGGGTGTTCT AGACTATTTT ATGGGTAAGA GGAATAGGAA GCCTTAGACC AAATTTCCCT

4141 CAAGTAGGTG TCCTTTCTCT CATTT
```

FIG.1D

```
  1 ATTCCCCCCCGCCCTCGCCGCCGCCACCACACACGCACGCTTCTCTCCATCTTGTGAT
 61 TCCTTTTTCCTCCTGAACCCTCCAGTGGGGGTGCGAGTTTGTCTTTATCACCCCCCATCC
121 CACCGCCTTCTTTTCTTCTCGCTCTCCTACCCCTCCCCAGCTTGGTGGGCGCCTCTTTCC
181 TTTCTCGCCCCCTTTCATTTTTATTTATTCATATTTATTTGGCGCCCGCTCTCTCTCTGT
241 CCCTTTGCCTGCCTCCCTCCCTCCGGATCCCCGCTCTCTCCCCGGAGTGGCGCGTCGGGG

301 GCTCCGCCGCTGGCCAGGCGTGATGTTGCACGTGGAGATGTTGACGCTGGTGTTTCTGGT
  1                       M  L  H  V  E  M  L  T  L  V  F  L  V

361 GCTCTGGATGTGTGTGTTCAGCCAGGACCCGGGCTCCAAGGCCGTCGCCGACCGCTACGC
 14  L  W  M  C  V  F  S  Q  D  P  G  S  K  A  V  A  D  R  Y  A

421 TGTCTACTGGAACAGCAGCAACCCCAGATTCCAGAGGGGTGACTACCATATTGATGTCTG
 34  V  Y  W  N  S  S  N  P  R  F  Q  R  G  D  Y  H  I  D  V  C

481 TATCAATGACTACCTGGATGTTTTCTGCCCTCACTATGAGGACTCCGTCCCAGAAGATAA
 54  I  N  D  Y  L  D  V  F  C  P  H  Y  E  D  S  V  P  E  D  K

541 GACTGAGCGCTATGTCCTCTACATGGTGAACTTTGATGGCTACAGTGCCTGCGACCACAC
 74  T  E  R  Y  V  L  Y  M  V  N  F  D  G  Y  S  A  C  D  H  T

601 TTCCAAAGGGTTCAAGAGATGGGAATGTAACCGGCCTCACTCTCCAAATGGACCGCTGAA
 94  S  K  G  F  K  R  W  E  C  N  R  P  H  S  P  N  G  P  L  K

661 GTTCTCTGAAAAATTCCAGCTCTTCACTCCCTTTTCTCTAGGATTTGAATTCAGGCCAGG
114  F  S  E  K  F  Q  L  F  T  P  F  S  L  G  F  E  F  R  P  G

721 CCGAGAATATTTCTACATCTCCTCTGCAATCCCAGATAATGGAAGAAGGTCCTGTCTAAA
134  R  E  Y  F  Y  I  S  S  A  I  P  D  N  G  R  R  S  C  L  K

781 GCTCAAAGTCTTTGTGAGACCAACAAATAGCTGTATGAAAACTATAGGTGTTCATGATCG
154  L  K  V  F  V  R  P  T  N  S  C  M  K  T  I  G  V  H  D  R

841 TGTTTTCGATGTTAACGACAAAGTAGAAAATTCATTAGAACCAGCAGATGACACCGTACA
174  V  F  D  V  N  D  K  V  E  N  S  L  E  P  A  D  D  T  V  H

901 TGAGTCAGCCGAGCCATCCCGCGGCGAGAACGCGGCACAAACACCAAGGATACCCAGCCG
194  E  S  A  E  P  S  R  G  E  N  A  A  Q  T  P  R  I  P  S  R

961 CCTTTTGGCAATCCTACTGTTCCTCCTGGCGATGCTTTTGACATTATAGCACAGTCTCCT
214  L  L  A  I  L  L  F  L  L  A  M  L  L  T  L  O

1021 CCCATCACTTGTCACAGAAAACATCAGGGTCTTGGAACACCAGAGATCCACCTAACTGCT
1081 CATCCTAAGAAGGGACTTGTTATTGGGTTTTGGCAGATGTCAGATTTTGGTTTTCTTTCT
1141 TTCAGCCTGAATTCTAAGCAACAACTTCAGGTTGGGGGCCTAAACTTGTTCCTGCCTCCC
1201 TCACCCCACCCCGCCCCACCCCCAGCCCTGGCCCTTGGCTTCTCTCACCCCTCCCAAATT
1261 AAATGGACTCCAGATGAAAATGCCAAATTGTCATAGTGACACCAGTGGTTCGTCAGCTCC
1321 TGTGCATTCTCCTCTAAGAACTCACCTCCGTTAGCGCACTGTGTCAGCGGGCTATGGACA
1381 AGGAAGAATAGTGGCAGATGCAGCCAGCGCTGGCTAGGGCTGGGAGGGTTTTGCTCTCCT
1441 ATGCAATATTTATGCCTTCTCATTCAGAACTGTAAGATGATCGCGCAGGGCATCATGTCA
1501 CCATGTCAGGTCCGGAGGGGAGGTATTAAGAATAGATACGATATTACACCATTTCCTATA
1561 GGAGTATGTAAATGAACAGGCTTCTAAAAGGTTGAGACACTGGNTTTTTTTTTTAATATG
1621 ACTGTCTTAAAGCATTCTTGACASCCCAACTTGTGCTCTCTAAAAGAAGCCTTTTTTTTT
1681 TTTCTAGGAGACAGAGTGGGTGTGGAATGCTAATACAGAGCAGGTGTGWAAACAGAGAAA
1741 ACTACAGGTTTGCTGGGGGTGTGTATGTGTGAGTGCCTCTAATTTTTTTGGTGACTGGGC
1801 AGTGCACACCAGATATTTTTTCTTTGAATACAGATCACG
```

FIG. 2

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
      (A) LENGTH: 4165 bases
      (B) TYPE: nucleic acid
      (C) STRANDEDNESS: single
      (D) TOPOLOGY: linear (xi) SEQUENCE DESCRIPTION: SEQ ID NO: 1:

AGCCCCCAGT CCTCTAGACA CTCTGCTTGC TTTTTCCCCG CTTCCCGCCG    50

```
CCTTTTTTTT TTTACGGAAA ACATCATCTA GATTTAAGAT GACTCGTCTT      100

CTTTAATCTC GTCCGTATCA GCACTGAAGA CTGAAAGGGA ACCTTCACCA      150

CCACTCCAAC CCTGGTGGGG GCTTAAAAAA AAAAAATAAC AGTTCTAAAA      200

AAGAAAGGGG GACCAAAAAA CAGAAAAAGG AAAGTCTTAA GAGGCAAAGG      250

AGCGGGACTC GGGACCCTCT GCAGACCCTT GACTCAGCCC ACCCAGGACC      300

GTACTAGCCA TCCGAACTTC TAATTCATCT TATCCAACTG AAAGGGAGGG      350

CGGCACAAGC CAGAAGCAAA CTTCGGCGGT CTCTGCGGAT CTGTGATTCC      400

CACATTGAGA GGGGTCGAGA GCCAGAAGGC ACAGGACCCC ACCAGGAGGA      450

GGAGTTCCGC GCCTCTCTCG CCCCTTCCAC CAAGCCTGAA CCTTAGACTG      500

AACCACGCGG GACCTAAGAG GCAGAAGAGG GTAGTAGAAA ATGCGGGGCT      550

CCGGGCCCCG CGGTGCGGGA CGCCGACGGA CCCAGGGCAG AGGTGGCGGC      600

GGCGACACCC CCCGCGTCCC TGCCTCTCTG GCAGGCTGCT ATTCCGCACC      650

TCTAAAGGGG CCCCTCTGGA CGTGCCTTCT CCTGTGTGCG GCGCTCCGGA      700

CCCTTTTGGC CAGCCCCAGT AACGAAGTGA ATTTATTGGA TTCGCGCACT      750

GTCCTGGGAG ACCTTGGATG GATTGCTTTT CCAAAGAATG GGTGGGAAGA      800

GATTGGTGAA GTTGATGAAA ACTATCCCCC CATCCACACC TATCAAGTGT      850

GCAAAGTTAT GGAACAGAAT CAGAATAATT GGCTGTTGAC CAGTTGGATC      900

TCTAACGAAG GTGCTTCCAG AATTTTTATT GAACTCAAGT TTACTCTGAG      950

GGATTGCAAC AGCCTTCCTG GAGGACTGGG GACTTGCAAG GAGACCTTTA     1000

ACATGTATTA TTTTGAGTCG GATGATGAGA ATGGGAGAAA TATCAAAGAG     1050

AACCAGTACA TCAAGATCGA TACCATTGCT GCTGATGAGA GCTTCACCGA     1100

ACTTGACCTT GGAGACCGGG TCATGAAGCT GAATACGGAG GTCAGAGATG     1150

TAGGACCTCT GAGCAAAAAG GGATTTTATC TTGCTTTCCA AGATGTCGGT     1200

GCTTGCATCG CTCTGGTTTC TGTCCGTGTC TACTATAAAA AATGTCCTTC     1250

TGTAGTTAGA CATTTGGCTG TTTTCCCTGA CACGATCACT GGAGCAGATT     1300

CTTCCCAGTT GCTAGAGGTG TCAGGCTCCT GCGTCAACCA TTCTGTGACA     1350

GACGATCCTC CCAAAATGCA TTGCAGTGCT GAAGGGGAGT GGCTGGTTCC     1400

CATCGGGAAA TGCATGTGCA AGGCCGGATA TGAAGAGAAA AATGGTACCT     1450

GTCAAGTGTG CAGACCTGGG TTCTTCAAAG CCTCTCCTCA CAGCCAGACC     1500

TGCAGCAAAT GTCCACCTCA CAGTTACACC CATGAGGAAG CTTCCACCTC     1550

TTGTGTCTGT GAAAAGGATT ATTTCAGGAG GGAATCTGAT CCGCCCACAA     1600

TGGCATGCAC AACTCCTTCT CCAGTCACCA ACGTGAAGAA GGGGAAGATC     1650

GCAAAGAACA GCATTTCTTT GTCTTGGCAA GAGCCAGATC GCCCCAATGG     1700

GATCATCCTG GAGTACGAAA TCAAGTACTT TGAAAAGGAC CAAGAGACCA     1750

GCTACACAAT TATCAAGTCT AAAGAGACCA CTATTACGGC AGAGGGCCTG     1800

AAACCTGCGT CTGTGTATGT CTTCCAAATT CGAGCACGTA CAGCAGCAGG     1850

CTACGGCGTC TTCAGTCGAC GGTTTGAGTT TGAAACCACA CCAGTGTCAG     1900

TTGCAGCATC TAATGATCAA AGCCAGATTC CCATCATTGC GGTGTCAGTG     1950

ACGGTGGGAG TCATCTTGTT GGCAGTGATG ATCGGCTTCC TCCTCAGTGG     2000
```

| | |
|---|---|
| CAGTTGCTGC GAATGTGGCT GTGGGAGGGC TTCTTCCCTG TGCGCTGTTG | 2050 |
| CCCATCCAAG CCTAATATGG CGGTGTGGCT ACAGCAAAGC AAAGCAGGAT | 2100 |
| CCAGAAGAGG AAAAGATGCA CTTTCATAAC GGGCACATTA AACTGCCAGG | 2150 |
| AGTAAGAACG TACATTGATC CACACACCTA CGAAGATCCC ACTCAAGCCG | 2200 |
| TTCATGAATT TGCCAAGGAG ATCGAGGCCT CATGCATCAC CATTGAGAGA | 2250 |
| GTTATTGGAG CAGGTGAATT TGGTGAAGTT TGTAGTGGAC GTTTGAAACT | 2300 |
| ACCCGGAAAA AGAGAATTGC CTGTGGCTAT CAAAACTCTT AAAGTAGGCT | 2350 |
| ACACTGAAAA GCAGCGCAGA GATTTTCTGA GTGAAGCGAG TATCATGGGG | 2400 |
| CAGTTTGATC ATCCAAACAT CATCCATCTA GAAGGCGTTG TGACTAAAAG | 2450 |
| TAAACCTGTG ATGATAGTGA CAGAGTACAT GGAGAATGGC TCCTTAGACA | 2500 |
| CATTTTTAAA GAAAAACGAT GGCCAGTTCA CTGTGATTCA GCTTGTTGGC | 2550 |
| ATGCTGAGAG GCATCGCTGC AGGAATGAAG TACCTTTCTG ACATGGGCTA | 2600 |
| CGTGCACAGA GACCTTGCTG CTAGAAACAT CTTAATCAAC AGTAACCTTG | 2650 |
| TGTGCAAAGT GTCTGACTTT GGACTTTCCA GGGTGCTGGA AGATGATCCT | 2700 |
| GAGGCAGCCT ATACCACAAG GGGAGGCAAA ATTCCAATCA GATGGACTGC | 2750 |
| TCCAGAAGCA ATAGCTTTTC GAAAGTTTAC CTCTGCCAGT GATGTCTGGA | 2800 |
| GCTATGGAAT CGTAATGTGG GAAGTTGTGT CCTATGGAGA GAGACCGTAC | 2850 |
| TGGGAGATGA CCAATCAGGA TGTGATCAAG GCAGTGGAAG AAGGCTACCG | 2900 |
| CCTGCCAAGC CCCATGGATT GTCCTGCTGC CCTCTATCAA TTAATGCTGG | 2950 |
| ATTGCTGGCA GAAAGATCGC AACAGCAGGC CCAAGTTTGA TGACATAGTC | 3000 |
| AACATGCTGG ATAAGCTGAT ACGAAACCCA AGTAGTTTGA AGACACTGGT | 3050 |
| GAACGCGTCA AGCAGGGTAT CTACTTTGTT GGCAGAACAT GGATCTTTGG | 3100 |
| GGTCTGGGGC CTACAGATCA GTAGGTGAAT GGCTAGAAGC AATCAAAATG | 3150 |
| GGCCGGTACA CAGAGATTTT CATGGAAAAT GGATACAGTT CAATGGACGC | 3200 |
| TGTGGCTCAG GTGACCTTGG AGGATTTGAG ACGCCTGGGA GTGACTCTGG | 3250 |
| TCGGTCACCA GAAGAAGATC ATGAACAGCC TTCAAGAGAT GAAGGTGCAG | 3300 |
| CTGGTAAACG GGATGGTGCC AGTGTGACCC GCACACGGGT CACTTCTCCA | 3350 |
| AGTGAACAAC TCTGCACTTT GTAAACAGCC CTAAGATTTA TTTTAACAGA | 3400 |
| GAAAGGGAAA TGGGTGGTTC CTAAACCTTT GAAGGCACTT GTCTCATCCT | 3450 |
| TTGACTTATA ATCAACATTT TACTAAAATC TCCAGATCTT CTTCTTAATG | 3500 |
| TCTTCGTTTT TTTCACTATG TAAATGTAAC CTGCGAAGAG AGCTAACATG | 3550 |
| AGAAACAACA TCCTATAAAA ACATAGTAAC TAAATCTTTC TCCACTTGCA | 3600 |
| GCCCCTTTCA AAACTACCAG GGATCGACTT GAAAGGAAAA GTTTTAAAGC | 3650 |
| CATGTGTGGG CAAAGAAACG CTGCATTTTA CTGACGTTTA CTTCGAGTTT | 3700 |
| TATTTGTCTG CATAAGTGTA TTGGAGAGCA ATATGATTAG ATTATTTCTT | 3750 |
| AAATACAGTT TGTAATTTAA AATGGAATTA CATGTTATAA GTTATAGAAA | 3800 |
| ATAGTTTACA GACATGTTGC CCGGTCAAGG AAAAGTTCAG CACAGGGTGT | 3850 |
| ATATTTATTT TTCTGTGTTA TATAATTTAC TTTTAGTTGC ACTTCTAGAG | 3900 |
| AGTATTAGGC AATGAATGTG TATAGACTGT ATAGTTTGCA ATATACCGAG | 3950 |
| GAATGGACTT AAATTGGAAA TGTATGTATA TGTGTGTGTA TGTGCGTATG | 4000 |

-continued

```
TGTGTGTGTG TTTGAATATG TAGATGGTAT TGTTCTGCTT GCCTTTTGTA         4050

TAGGGTTTTA ATTTTGGCCT CATACAGCAA AGGGTGTTCT AGACTATTTT         4100

ATGGGTAAGA GGAATAGGAA GCCTTAGACC AAATTTCCCT CAAGTAGGTG         4150

TCCTTTCTCT CATTT                                               4165
```

(2) INFORMATION FOR SEQ ID NO: 2:

(i) SEQUENCE CHARACTERISTICS:
        (A) LENGTH: 928 amino acids
        (B) TYPE: amino acid
        (D) TOPOLOGY: linear (xi) SEQUENCE DESCRIPTION: SEQ ID NO: 2:

```
Met Arg Gly Ser Gly Pro Arg Gly Ala Gly Arg Arg Thr Gln
 1               5                  10                  15

Gly Arg Gly Gly Gly Asp Thr Pro Arg Val Pro Ala Ser Leu
                20                  25                  30

Ala Gly Cys Tyr Ser Ala Pro Leu Lys Gly Pro Leu Trp Thr Cys
                35                  40                  45

Leu Leu Leu Cys Ala Ala Leu Arg Thr Leu Leu Ala Ser Pro Ser
                50                  55                  60

Asn Glu Val Asn Leu Leu Asp Ser Arg Thr Val Leu Gly Asp Leu
                65                  70                  75

Gly Trp Ile Ala Phe Pro Lys Asn Gly Trp Glu Glu Ile Gly Glu
                80                  85                  90

Val Asp Glu Asn Tyr Pro Pro Ile His Thr Tyr Gln Val Cys Lys
                95                  100                 105

Val Met Glu Gln Asn Gln Asn Asn Trp Leu Leu Thr Ser Trp Ile
                110                 115                 120

Ser Asn Glu Gly Ala Ser Arg Ile Phe Ile Glu Leu Lys Phe Thr
                125                 130                 135

Leu Arg Asp Cys Asn Ser Leu Pro Gly Gly Leu Gly Thr Cys Lys
                140                 145                 150

Glu Thr Phe Asn Met Tyr Tyr Phe Glu Ser Asp Asp Glu Asn Gly
                155                 160                 165

Arg Asn Ile Lys Glu Asn Gln Tyr Ile Lys Ile Asp Thr Ile Ala
                170                 175                 180

Ala Asp Glu Ser Phe Thr Glu Leu Asp Leu Gly Asp Arg Val Met
                185                 190                 195

Lys Leu Asn Thr Glu Val Arg Asp Val Gly Pro Leu Ser Lys Lys
                200                 205                 210

Gly Phe Tyr Leu Ala Phe Gln Asp Val Gly Ala Cys Ile Ala Leu
                215                 220                 225

Val Ser Val Arg Val Tyr Tyr Lys Lys Cys Pro Ser Val Val Arg
                230                 235                 240

His Leu Ala Val Phe Pro Asp Thr Ile Thr Gly Ala Asp Ser Ser
                245                 250                 255

Gln Leu Leu Glu Val Ser Gly Ser Cys Val Asn His Ser Val Thr
                260                 265                 270

Asp Asp Pro Pro Lys Met His Cys Ser Ala Glu Gly Glu Trp Leu
                275                 280                 285

Val Pro Ile Gly Lys Cys Met Cys Lys Ala Gly Tyr Glu Glu Lys
                290                 295                 300
```

-continued

```
Asn Gly Thr Cys Gln Val Cys Arg Pro Gly Phe Phe Lys Ala Ser
            305                 310                 315
Pro His Ser Gln Thr Cys Ser Lys Cys Pro Pro His Ser Tyr Thr
            320                 325                 330
His Glu Glu Ala Ser Thr Ser Cys Val Cys Glu Lys Asp Tyr Phe
            335                 340                 345
Arg Arg Glu Ser Asp Pro Pro Thr Met Ala Cys Thr Thr Pro Ser
            350                 355                 360
Pro Val Thr Asn Val Lys Lys Gly Lys Ile Ala Lys Asn Ser Ile
            365                 370                 375
Ser Leu Ser Trp Gln Glu Pro Asp Arg Pro Asn Gly Ile Ile Leu
            380                 385                 390
Glu Tyr Glu Ile Lys Tyr Phe Glu Lys Asp Gln Glu Thr Ser Tyr
            395                 400                 405
Thr Ile Ile Lys Ser Lys Glu Thr Thr Ile Thr Ala Glu Gly Leu
            410                 415                 420
Lys Pro Ala Ser Val Tyr Val Phe Gln Ile Arg Ala Arg Thr Ala
            425                 430                 435
Ala Gly Tyr Gly Val Phe Ser Arg Arg Phe Glu Phe Glu Thr Thr
            440                 445                 450
Pro Val Ser Val Ala Ala Ser Asn Asp Gln Ser Gln Ile Pro Ile
            455                 460                 465
Ile Ala Val Ser Val Thr Val Gly Val Ile Leu Leu Ala Val Met
            470                 475                 480
Ile Gly Phe Leu Leu Ser Gly Ser Cys Cys Glu Cys Gly Cys Gly
            485                 490                 495
Arg Ala Ser Ser Leu Cys Ala Val Ala His Pro Ser Leu Ile Trp
            500                 505                 510
Arg Cys Gly Tyr Ser Lys Ala Lys Gln Asp Pro Glu Glu Glu Lys
            515                 520                 525
Met His Phe His Asn Gly His Ile Lys Leu Pro Gly Val Arg Thr
            530                 535                 540
Tyr Ile Asp Pro His Thr Tyr Glu Asp Pro Thr Gln Ala Val His
            545                 550                 555
Glu Phe Ala Lys Glu Ile Glu Ala Ser Cys Ile Thr Ile Glu Arg
            560                 565                 570
Val Ile Gly Ala Gly Glu Phe Gly Glu Val Cys Ser Gly Arg Leu
            575                 580                 585
Lys Leu Pro Gly Lys Arg Glu Leu Pro Val Ala Ile Lys Thr Leu
            590                 595                 600
Lys Val Gly Tyr Thr Glu Lys Gln Arg Arg Asp Phe Leu Ser Glu
            605                 610                 615
Ala Ser Ile Met Gly Gln Phe Asp His Pro Asn Ile Ile His Leu
            620                 625                 630
Glu Gly Val Val Thr Lys Ser Lys Pro Val Met Ile Val Thr Glu
            635                 640                 645
Tyr Met Glu Asn Gly Ser Leu Asp Thr Phe Leu Lys Lys Asn Asp
            650                 655                 660
Gly Gln Phe Thr Val Ile Gln Leu Val Gly Met Leu Arg Gly Ile
            665                 670                 675
Ala Ala Gly Met Lys Tyr Leu Ser Asp Met Gly Tyr Val His Arg
            680                 685                 690
Asp Leu Ala Ala Arg Asn Ile Leu Ile Asn Ser Asn Leu Val Cys
```

```
                        695                 700                 705
Lys Val Ser Asp Phe Gly Leu Ser Arg Val Leu Glu Asp Pro
            710                 715                 720
Glu Ala Ala Tyr Thr Thr Arg Gly Gly Lys Ile Pro Ile Arg Trp
            725                 730                 735
Thr Ala Pro Glu Ala Ile Ala Phe Arg Lys Phe Thr Ser Ala Ser
            740                 745                 750
Asp Val Trp Ser Tyr Gly Ile Val Met Trp Glu Val Val Ser Tyr
            755                 760                 765
Gly Glu Arg Pro Tyr Trp Glu Met Thr Asn Gln Asp Val Ile Lys
            770                 775                 780
Ala Val Glu Glu Gly Tyr Arg Leu Pro Ser Pro Met Asp Cys Pro
            785                 790                 795
Ala Ala Leu Tyr Gln Leu Met Leu Asp Cys Trp Gln Lys Asp Arg
            800                 805                 810
Asn Ser Arg Pro Lys Phe Asp Asp Ile Val Asn Met Leu Asp Lys
            815                 820                 825
Leu Ile Arg Asn Pro Ser Ser Leu Lys Thr Leu Val Asn Ala Ser
            830                 835                 840
Ser Arg Val Ser Thr Leu Leu Ala Glu His Gly Ser Leu Gly Ser
            845                 850                 855
Gly Ala Tyr Arg Ser Val Gly Glu Trp Leu Glu Ala Ile Lys Met
            860                 865                 870
Gly Arg Tyr Thr Glu Ile Phe Met Glu Asn Gly Tyr Ser Ser Met
            875                 880                 885
Asp Ala Val Ala Gln Val Thr Leu Glu Asp Leu Arg Arg Leu Gly
            890                 895                 900
Val Thr Leu Val Gly His Gln Lys Lys Ile Met Asn Ser Leu Gln
            905                 910                 915
Glu Met Lys Val Gln Leu Val Asn Gly Met Val Pro Val
            920                 925             928

(2) INFORMATION FOR SEQ ID NO: 3:

(i) SEQUENCE CHARACTERISTICS:
        (A) LENGTH: 1839 bases
        (B) TYPE: nucleic acid
        (C) STRANDEDNESS: single
        (D) TOPOLOGY: linear (xi) SEQUENCE DESCRIPTION: SEQ ID NO: 3:

ATTCCCCCCC GCCCTCGCCG CCGCCACCAC ACACACGCAC GCTTCTCTCC           50

ATCTTGTGAT TCCTTTTTCC TCCTGAACCC TCCAGTGGGG GTGCGAGTTT          100

GTCTTTATCA CCCCCCATCC CACCGCCTTC TTTTCTTCTC GCTCTCCTAC          150

CCCTCCCCAG CTTGGTGGGC GCCTCTTTCC TTTCTCGCCC CCTTTCATTT          200

TTATTTATTC ATATTTATTT GGCGCCCGCT CTCTCTCTGT CCCTTTGCCT          250

GCCTCCCTCC CTCCGGATCC CCGCTCTCTC CCCGGAGTGG CGCGTCGGGG          300

GCTCCGCCGC TGGCCAGGCG TGATGTTGCA CGTGGAGATG TTGACGCTGG          350

TGTTTCTGGT GCTCTGGATG TGTGTGTTCA GCCAGGACCC GGGCTCCAAG          400

GCCGTCGCCG ACCGCTACGC TGTCTACTGG AACAGCAGCA ACCCCAGATT          450

CCAGAGGGGT GACTACCATA TTGATGTCTG TATCAATGAC TACCTGGATG          500

TTTTCTGCCC TCACTATGAG GACTCCGTCC CAGAAGATAA GACTGAGCGC          550
```

-continued

| | |
|---|---|
| TATGTCCTCT ACATGGTGAA CTTTGATGGC TACAGTGCCT GCGACCACAC | 600 |
| TTCCAAAGGG TTCAAGAGAT GGGAATGTAA CCGGCCTCAC TCTCCAAATG | 650 |
| GACCGCTGAA GTTCTCTGAA AAATTCCAGC TCTTCACTCC CTTTTCTCTA | 700 |
| GGATTTGAAT TCAGGCCAGG CCGAGAATAT TTCTACATCT CCTCTGCAAT | 750 |
| CCCAGATAAT GGAAGAAGGT CCTGTCTAAA GCTCAAAGTC TTTGTGAGAC | 800 |
| CAACAAATAG CTGTATGAAA ACTATAGGTG TTCATGATCG TGTTTTCGAT | 850 |
| GTTAACGACA AAGTAGAAAA TTCATTAGAA CCAGCAGATG ACACCGTACA | 900 |
| TGAGTCAGCC GAGCCATCCC GCGGCGAGAA CGCGGCACAA ACACCAAGGA | 950 |
| TACCCAGCCG CCTTTTGGCA ATCCTACTGT TCCTCCTGGC GATGCTTTTG | 1000 |
| ACATTATAGC ACAGTCTCCT CCCATCACTT GTCACAGAAA ACATCAGGGT | 1050 |
| CTTGGAACAC CAGAGATCCA CCTAACTGCT CATCCTAAGA AGGGACTTGT | 1100 |
| TATTGGGTTT TGGCAGATGT CAGATTTTGG TTTTCTTTCT TTCAGCCTGA | 1150 |
| ATTCTAAGCA ACAACTTCAG GTTGGGGGCC TAAACTTGTT CCTGCCTCCC | 1200 |
| TCACCCCACC CCGCCCCACC CCCAGCCCTG GCCCTTGGCT TCTCTCACCC | 1250 |
| CTCCCAAATT AAATGGACTC CAGATGAAAA TGCCAAATTG TCATAGTGAC | 1300 |
| ACCAGTGGTT CGTCAGCTCC TGTGCATTCT CCTCTAAGAA CTCACCTCCG | 1350 |
| TTAGCGCACT GTGTCAGCGG GCTATGGACA AGGAAGAATA GTGGCAGATG | 1400 |
| CAGCCAGCGC TGGCTAGGGC TGGGAGGGTT TTGCTCTCCT ATGCAATATT | 1450 |
| TATGCCTTCT CATTCAGAAC TGTAAGATGA TCGCGCAGGG CATCATGTCA | 1500 |
| CCATGTCAGG TCCGGAGGGG AGGTATTAAG AATAGATACG ATATTACACC | 1550 |
| ATTTCCTATA GGAGTATGTA AATGAACAGG CTTCTAAAAG GTTGAGACAC | 1600 |
| TGGNTTTTTT TTTTAATATG ACTGTCTTAA AGCATTCTTG ACASCCCAAC | 1650 |
| TTGTGCTCTC TAAAAGAAGC CTTTTTTTTT TTTCTAGGAG ACAGAGTGGG | 1700 |
| TGTGGAATGC TAATACAGAG CAGGTGTGWA AACAGAGAAA ACTACAGGTT | 1750 |
| TGCTGGGGGT GTGTATGTGT GAGTGCCTCT AATTTTTTTG GTGACTGGGC | 1800 |
| AGTGCACACC AGATATTTTT TCTTTGAATA CAGATCACG | 1839 |

(2) INFORMATION FOR SEQ ID NO: 4:

(i) SEQUENCE CHARACTERISTICS:
        (A) LENGTH: 228 amino acids
        (B) TYPE: amino acid
        (D) TOPOLOGY: linear (xi) SEQUENCE DESCRIPTION: SEQ ID NO: 4:

```
Met Leu His Val Glu Met Leu Thr Leu Val Phe Leu Val Leu Trp
 1               5                  10                  15

Met Cys Val Phe Ser Gln Asp Pro Gly Ser Lys Ala Val Ala Asp
                20                  25                  30

Arg Tyr Ala Val Tyr Trp Asn Ser Ser Asn Pro Arg Phe Gln Arg
                35                  40                  45

Gly Asp Tyr His Ile Asp Val Cys Ile Asn Asp Tyr Leu Asp Val
                50                  55                  60

Phe Cys Pro His Tyr Glu Asp Ser Val Pro Glu Asp Lys Thr Glu
                65                  70                  75

Arg Tyr Val Leu Tyr Met Val Asn Phe Asp Gly Tyr Ser Ala Cys
```

```
                80              85              90
Asp His Thr Ser Lys Gly Phe Lys Arg Trp Glu Cys Asn Arg Pro
                    95              100             105
His Ser Pro Asn Gly Pro Leu Lys Phe Ser Glu Lys Phe Gln Leu
                    110             115             120
Phe Thr Pro Phe Ser Leu Gly Phe Glu Phe Arg Pro Gly Arg Glu
                    125             130             135
Tyr Phe Tyr Ile Ser Ser Ala Ile Pro Asp Asn Gly Arg Arg Ser
                    140             145             150
Cys Leu Lys Leu Lys Val Phe Val Arg Pro Thr Asn Ser Cys Met
                    155             160             165
Lys Thr Ile Gly Val His Asp Arg Val Phe Asp Val Asn Asp Lys
                    170             175             180
Val Glu Asn Ser Leu Glu Pro Ala Asp Asp Thr Val His Glu Ser
                    185             190             195
Ala Glu Pro Ser Arg Gly Glu Asn Ala Ala Gln Thr Pro Arg Ile
                    200             205             210
Pro Ser Arg Leu Leu Ala Ile Leu Leu Phe Leu Leu Ala Met Leu
                    215             220             225
Leu Thr Leu
        228

(2) INFORMATION FOR SEQ ID NO: 5:

(i) SEQUENCE CHARACTERISTICS:
        (A) LENGTH: 37 bases
        (B) TYPE: nucleic acid
        (C) STRANDEDNESS: single
        (D) TOPOLOGY: linear (xi) SEQUENCE DESCRIPTION: SEQ ID NO: 5:

CCCTCGAGGT CGACCAYMGN GAYYTNGCNR CNMGNAA                    37

(2) INFORMATION FOR SEQ ID NO: 6:

(i) SEQUENCE CHARACTERISTICS:
        (A) LENGTH: 37 bases
        (B) TYPE: nucleic acid
        (C) STRANDEDNESS: single
        (D) TOPOLOGY: linear (xi) SEQUENCE DESCRIPTION: SEQ ID NO: 6:

CCCTCGAGGT CGACCAYMGN GAYYTNGCNT GYMGNAA                    37

(2) INFORMATION FOR SEQ ID NO: 7:

(i) SEQUENCE CHARACTERISTICS:
        (A) LENGTH: 31 bases
        (B) TYPE: nucleic acid
        (C) STRANDEDNESS: single
        (D) TOPOLOGY: linear (xi) SEQUENCE DESCRIPTION: SEQ ID NO: 7:

CCGCGGTGCG GCCGCCRWAN SHCCANACRT C                          31

(2) INFORMATION FOR SEQ ID NO: 8:

(i) SEQUENCE CHARACTERISTICS:
        (A) LENGTH: 21 bases
        (B) TYPE: nucleic acid
        (C) STRANDEDNESS: single
        (D) TOPOLOGY: linear
```

(xi) SEQUENCE DESCRIPTION: SEQ ID NO: 8:

TCTGTGACAG ACGATCCTCC C                                        21

(2) INFORMATION FOR SEQ ID NO: 9:

(i) SEQUENCE CHARACTERISTICS:
        (A) LENGTH: 54 bases
        (B) TYPE: nucleic acid
        (C) STRANDEDNESS: single
        (D) TOPOLOGY: linear (xi) SEQUENCE DESCRIPTION: SEQ ID NO: 9:

GCACGGTGGA CATGTGTGAG TTTTGTCCTG GCTTTGATCA TTAGATGCTG          50

CAAC                                                           54

(2) INFORMATION FOR SEQ ID NO: 10:

(i) SEQUENCE CHARACTERISTICS:
        (A) LENGTH: 54 bases
        (B) TYPE: nucleic acid
        (C) STRANDEDNESS: single
        (D) TOPOLOGY: linear (xi) SEQUENCE DESCRIPTION: SEQ ID NO: 10:

GTTGCAGCAT CTAATGATCA AAGCCAGGAC AAAACTCACA CATGTCCACC          50

GTGC                                                           54

(2) INFORMATION FOR SEQ ID NO: 11:

(i) SEQUENCE CHARACTERISTICS:
        (A) LENGTH: 18 bases
        (B) TYPE: nucleic acid
        (C) STRANDEDNESS: single
        (D) TOPOLOGY: linear (xi) SEQUENCE DESCRIPTION: SEQ ID NO: 11:

GCACTTGTAC TCCTTGCC                                            18

(2) INFORMATION FOR SEQ ID NO: 12:

(i) SEQUENCE CHARACTERISTICS:
        (A) LENGTH: 28 amino acids
        (B) TYPE: amino acid
        (D) TOPOLOGY: linear (xi) SEQUENCE DESCRIPTION: SEQ ID NO: 12:

Asp Arg Tyr Ala Val Tyr Trp Asn Ser Ser Asn Pro Arg Phe Gln
  1               5                  10                  15

Arg Gly Asp Tyr His Asn Asp Val Xaa Asn Asn Asp Tyr
             20                  25          28

(2) INFORMATION FOR SEQ ID NO: 13:

(i) SEQUENCE CHARACTERISTICS:
        (A) LENGTH: 24 amino acids
        (B) TYPE: amino acid
        (D) TOPOLOGY: linear (xi) SEQUENCE DESCRIPTION: SEQ ID NO: 13:

Met Lys Thr Asn Gly Val His Asp Arg Val Phe Asp Val Asn Asp
  1               5                  10                  15

Lys Val Glu Asn Xaa Leu Glu Pro Ala
             20              24

(2) INFORMATION FOR SEQ ID NO: 14:

(i) SEQUENCE CHARACTERISTICS:
        (A) LENGTH: 23 amino acids
        (B) TYPE: amino acid
        (D) TOPOLOGY: linear (xi) SEQUENCE DESCRIPTION: SEQ ID NO: 14:

```
Val Asn Phe Asp Gly Tyr Ser Ala Xaa Asp His Thr Ser Lys Gly
 1               5                  10                  15

Phe Lys Arg Xaa Glu Xaa Asn Arg
            20          23
```

(2) INFORMATION FOR SEQ ID NO: 15:

(i) SEQUENCE CHARACTERISTICS:
        (A) LENGTH: 27 amino acids
        (B) TYPE: amino acid
        (D) TOPOLOGY: linear (xi) SEQUENCE DESCRIPTION: SEQ ID NO: 15:

```
Phe Gln Leu Phe Thr Pro Phe Ser Leu Gly Xaa Glu Xaa Arg Xaa
 1               5                  10                  15

Gly Arg Glu Xaa Phe Tyr Asn Ser Xaa Ala Asn Pro
            20              25      27
```

(2) INFORMATION FOR SEQ ID NO: 16:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 16:

```
Lys Arg Trp Glu Cys Asn Arg Pro
 1               5           8
```

(2) INFORMATION FOR SEQ ID NO: 17:

(i) SEQUENCE CHARACTERISTICS:
        (A) LENGTH: 37 bases
        (B) TYPE: nucleic acid
        (C) STRANDEDNESS: single
        (D) TOPOLOGY: linear (xi) SEQUENCE DESCRIPTION: SEQ ID NO: 17:

CCCTCGAGGT CGACGAYMGN TAYGCNGTNT AYTGGAA                 37

(2) INFORMATION FOR SEQ ID NO: 18:

(i) SEQUENCE CHARACTERISTICS:
        (A) LENGTH: 42 bases
        (B) TYPE: nucleic acid
        (C) STRANDEDNESS: single
        (D) TOPOLOGY: linear (xi) SEQUENCE DESCRIPTION: SEQ ID NO: 18:

CCGCGGTGCG GCCGCTCTAG ARTANCCRTC RAARTTNACC AT           42

AL-1 NEUROTROPHIC FACTOR TREATMENTS

This is a continuation of co-pending application(s) Ser. No. 08/330,128 filed on Oct. 27, 1994, which application(s) is (are) incorporated herein by reference and to which application(s) priority is claimed under 35 USC §120.

FIELD OF THE INVENTION

This application relates to the production of polypeptides involved in neuronal survival and/or growth, in particular the production of purified forms thereof by means of recombinant DNA technology.

BACKGROUND OF THE INVENTION

A number of protein neurotrophic factors, or neurotrophins, have been identified which influence growth and development of the vertebrate nervous system. It is believed that these factors play an important role in promoting the differentiation, survival, and function of diverse groups of neurons in the brain and periphery.

The belief that neurotrophic factors have important signalling functions in neural tissues is based upon the precedent established by work with nerve growth factor (NGF). NGF has been shown, both in vitro and in vivo, to support the survival of sympathetic, sensory, and basal forebrain neurons. Administration of exogenous NGF rescues neurons from cell death during development. Conversely, removal or sequestration of endogenous NGF by administration of anti-NGF antibodies promotes such cell death. Heumann, J. Exp. Biol. 132:133–150 (1987); Hefti, J. Neurosci. 6:2155–2162 (1986); Thoenen and Barde, Annu. Rev. Physiol. 60:284–335 (1980).

Additional neurotrophic factors related to NGF have since been identified. These include brain-derived neurotrophic factor (BDNF) (Leibrock, et al., Nature 341:149–152 (1989)), neurotrophin-3 (NT-3) (Kaisho, et al., FEBS Lett. 266:187 (1990); Maisonpierre, et al., Science 247:1446 (1990); Rosenthal, et al., Neuron 4:767 (1990)), and neurotrophin 4/5 (NT-4/5) (Berkmeier, et al., Neuron 7:857–866 (1991)).

Neurotrophins, similar to other polypeptide growth factors, affect their target cells through interactions with cell surface receptors. According to our current understanding, two kinds of transmembrane glycoproteins act as receptors for the known neurotrophins. Equilibrium binding studies have shown that neurotrophin-responsive neuronal cells possess a common low molecular weight (65,000–80,000 Daltons), low affinity receptor, typically referred to as $p75^{LNGFR}$ or p75, and high molecular weight (130,000–150,000 Daltons), high and low affinity receptors that are members of the trk family of receptor tyrosine kinases.

Receptor tyrosine kinases are known to serve as receptors for a variety of protein factors that promote cellular proliferation, differentiation, and survival. In addition to the trk receptors, examples of other receptor tyrosine kinases include the receptors for epidermal growth factor (EGF), fibroblast growth factor (FGF), and platelet-derived growth factor (PDGF). Typically, these receptors span the cell membrane, with one portion of the receptor being intracellular and in contact with the cytoplasm, and another portion of the receptor being extracellular. Binding of a ligand to the extracellular portion of the receptor is believed to induce tyrosine kinase activity in the intracellular portion of the receptor, with ensuing phosphorylation of various intracellular proteins involved in cellular signalling pathways.

In addition to receptor tyrosine kinases that serve as receptors for known protein factors, many receptor-like tyrosine kinases have been identified for which no ligand is known. Examples of such "orphan" receptors include recently discovered members of the eph family, which includes eph, elk, cek5, cek7, mek4/cek4/hek, sek, hek2, and bsk (Tuzi, et al., Br. J. Cancer 69:417–421 (1994); Zhou, et al., J. Neurosci. Res. 37:129–143 (1994)). Recently, a protein ligand has been identified for another eph family member, eck (Bartley, et al., Nature 368:558–560 (1994)).

Although eph family members are expressed in many different tissues, several family members are expressed in the nervous system or specifically in neurons (Maisonpierre, et al., Oncogene 8:3277–3288 (1993); Lai, et al., Neuron 6:691–704 (1991). In order to better understand the role of these and other orphan receptor tyrosine kinases in the nervous system, it would be useful to identify new ligands that bind to such receptors.

The present invention is based on successful research resulting in the identification, cloning, and sequencing of an eph-related tyrosine kinase receptor, referred to as REK7, and its ligand, referred to as AL-1.

It is an object of the present invention to provide nucleic acid encoding AL-1, and to use the nucleic acid to produce AL-1 in recombinant host cells for diagnostic use or for therapeutic use.

It is another object to use such nucleic acids encoding AL-1, and portions thereof, to identify related nucleic acids in the cells or tissues of various animal species.

It is another object to provide derivatives and modified forms of AL-1, including amino acid sequence variants and covalent derivatives thereof, as well as antagonists of AL-1.

It is another object to prepare immunogens for raising antibodies, as well as to obtain antibodies, capable of binding to AL-1, or derivatives or modified forms thereof.

These and other objects of the invention will be apparent to the ordinary artisan upon consideration of the specification as a whole.

SUMMARY OF THE INVENTION

These objects are accomplished by first providing isolated DNA comprising the nucleotide coding sequence for AL-1, an expression vector comprising the nucleotide coding sequence for AL-1, host cells transformed with the vector, including mammalian and bacterial host cells, and a method of using a nucleic acid molecule encoding AL-1 to effect the production of AL-1, comprising culturing a host cell transfected to express such nucleic acid molecule and recovering AL-1 from the host cell culture. In this method, preferably the host cell is transfected with an expression vector comprising the nucleotide coding sequence for AL-1.

By providing the full nucleotide coding sequence for AL-1, the invention enables the production of AL-1 by means of recombinant DNA technology, thereby making available for the first time sufficient quantities of substantially pure AL-1 protein for diagnostic and therapeutic uses with a variety of neurological disorders. In a preferred embodiment, the invention provides AL-1 that is free of other human proteins.

Modified and variant forms of AL-1 are produced in vitro by means of chemical or enzymatic treatment or in vivo by means of recombinant DNA technology. Such polypeptides differ from native AL-1, for example, by virtue of one or more amino acid substitutions, deletions or insertions, or in the extent or pattern of glycosylation, but substantially retain a biological activity of native AL-1.

Antibodies to AL-1 are produced by immunizing an animal with AL-1 or a fragment thereof, optionally in conjunction with an immunogenic polypeptide, and thereafter recovering antibodies from the serum of the immunized animals. Alternatively, monoclonal antibodies are prepared from cells of the immunized animal in conventional fashion. Antibodies obtained by routine screening will bind to AL-1 but will not substantially bind to (i.e., cross react with) NGF, BDNF, NT-3, NT-4/5, or other neurotrophic factors. Immobilized anti-AL-1 antibodies are particularly useful in the detection of AL-1 in clinical samples for diagnostic purposes, and in the purification of AL-1.

AL-1, its derivatives, or its antibodies are formulated with physiologically acceptable carriers, especially for therapeutic use. Such carriers are used, for example, to provide sustained-release formulations of AL-1.

In further aspects, the invention provides a method for determining the presence of a nucleic acid molecule encoding AL-1 in test samples prepared from cells, tissues, or biological fluids, comprising contacting the test sample with isolated DNA comprising all or a portion of the nucleotide coding sequence for AL-1 and determining whether the isolated DNA hybridizes to a nucleic acid molecule in the test sample. DNA comprising all or a portion of the nucleotide coding sequence for AL-1 is also used in hybridization assays to identify and to isolate nucleic acids sharing substantial sequence identity to the coding sequence for AL-1, such as nucleic acids that encode allelic variants of AL-1.

Also provided is a method for amplifying a nucleic acid molecule encoding AL-1 that is present in a test sample, comprising the use of an oligonucleotide having a portion of the nucleotide coding sequence for AL-1 as a primer in a polymerase chain reaction.

BRIEF DESCRIPTION OF THE DRAWINGS

FIGS. 1A–1D show the nucleotides coding sequence (SEQ, ID. NO: 1), and the deduced amino acid sequence (SEQ. ID. NO: 2) encoded by the isolated REK7 cDNA. The N-terminus of the mature REK7 protein is indicated by a rightward arrow and the C-terminus of the REK7 extracellular domain is indicated by a vertical arrow.

FIG. 2 shows the nucleotide coding sequence (SEQ. ID. NO: 3), and the deduced amino acid sequence (SEQ. ID. NO: 4) encoded by the isolated AL-1 cDNA. The N-terminus of the mature AL-1 protein is indicated by a rightward arrow (the mature protein begins with amino acid residue number 21). The underlined sequences corresponds to the sequences obtained by sequencing of purified BT20 cell-derived AL-1. The shaded boxes indicate potential N-glycosylation sites. The unshaded box shows the C-terminal hydrophobic domain and the upward arrow indicates a potential attachment site for glycophosphatidyl-inositol (GPI).

DETAILED DESCRIPTION OF THE PREFERRED EMBODIMENTS

"AL-1" or "AL-1 protein" refers to a polypeptide or protein encoded by the AL-1 nucleotide sequence set forth in FIG. 2 (SEQ ID NO: 3); a polypeptide that is the translated amino acid sequence set forth in FIG. 2 (SEQ ID NO: 4); fragments thereof having greater than about 5 amino acid residues and comprising an immune epitope or other biologically active site of AL-1; amino acid sequence variants of the amino acid sequence set forth in FIG. 2 (SEQ ID NO: 4) wherein one or more amino acid residues are added at the N- or C-terminus of, or within, said FIG. 2 (SEQ ID NO: 4) sequence or its fragments as defined above; amino acid sequence variants of said FIG. 2 (SEQ ID NO: 4) sequence or its fragments as defined above wherein one or more amino acid residues of said FIG. 2 (SEQ ID NO: 4) sequence or fragment thereof are deleted, and optionally substituted by one or more amino acid residues; and derivatives of the above proteins, polypeptides, or fragments thereof, wherein an amino acid residue has been covalently modified so that the resulting product is a non-naturally occurring amino acid. AL-1 amino acid sequence variants may be made synthetically, for example, by site-directed or PCR mutagenesis, or may exist naturally, as in the case of allelic forms and other naturally occurring variants of the translated amino acid sequence set forth in FIG. 2 (SEQ ID NO: 4) that may occur in human and other animal species. In any event, such fragments, variants, and derivatives exclude any polypeptide heretofore identified, including any known neurotrophic factor, such as nerve growth factor (NGF), brain derived neurotrophic factor (BDNF), neurotrophin-3 (NT-3), and neurotrophin-4/5 (NT-4/5), as well as statutorily obvious variants thereof.

An AL-1 amino acid sequence variant is included within the scope of the invention provided that it is functionally active. As used herein, "functionally active" and "functional activity" in reference to AL-1 means that the AL-1 is able to promote the growth, survival, and/or differentiation of neurons, especially axon fasciculation, whether the neurons be central, peripheral, or motorneurons, and/or that the AL-1 is immunologically cross-reactive with an antibody directed against an epitope of naturally occurring AL-1. Therefore, AL-1 amino acid sequence variants generally will share at least about 75% (preferably greater than 80% and more preferably greater than 90%) sequence identity with the translated amino acid sequence set forth in FIG. 2 (SEQ ID NO: 4), after aligning the sequences to provide for maximum homology, as determined, for example, by the Fitch, et al., Proc. Nat. Acad. Sci. USA 80:1382–1386 (1983), version of the algorithm described by Needleman, et al., J. Mol. Biol. 48:443–453 (1970).

Amino acid sequence variants of AL-1 are prepared by introducing appropriate nucleotide changes into AL-1 DNA and thereafter expressing the resulting modified DNA in a host cell, or by in vitro synthesis. Such variants include, for example, deletions from, or insertions or substitutions of, amino acid residues within the AL-1 amino acid sequence set forth in FIG. 2 (SEQ ID NO: 4). Any combination of deletion, insertion, and substitution may be made to arrive at an amino acid sequence variant of AL-1, provided that such variant possesses the desired characteristics described herein. Changes that are made in the amino acid sequence set forth in FIG. 2 (SEQ ID NO: 4) to arrive at an amino acid sequence variant of AL-1 also may result in further modifications of AL-1 upon its expression in host cells, for example, by virtue of such changes introducing or moving sites of glycosylation, or introducing membrane anchor sequences as described, for example, in PCT Pat. Pub. No. WO 89/01041 (published February 9, 1989).

There are two principal variables in the construction of amino acid sequence variants of AL-1: the location of the mutation site and the nature of the mutation. These are variants from the amino acid sequence set forth in FIG. 2 (SEQ ID NO: 4), and may represent naturally occurring allelic forms of AL-1, or predetermined mutant forms of AL-1 made by mutating AL-1 DNA, either to arrive at an allele or a variant not found in nature. In general, the location and nature of the mutation chosen will depend upon the AL-1 characteristic to be modified.

For example, due to the degeneracy of nucleotide coding sequences, mutations can be made in the AL-1 nucleotide sequence set forth in FIG. 2 (SEQ ID NO: 3) without affecting the amino acid sequence of the AL-1 encoded thereby. Other mutations can be made that will result in a AL-1 that has an amino acid sequence different from that set forth in FIG. 2 (SEQ ID NO: 4), but which is functionally active. Such functionally active amino acid sequence variants of AL-1 are selected, for example, by substituting one or more amino acid residues in the amino acid sequence set forth in FIG. 2 (SEQ ID NO: 4) with other amino acid residues of a similar or different polarity or charge.

One useful approach is called "alanine scanning mutagenesis." Here, a an amino acid residue or group of target residues are identified (e.g., charged residues such as arg, asp, his, lys, and glu) and, by means of recombinant DNA technology, replaced by a neutral or negatively charged amino acid (most preferably alanine or polyalanine) to affect the interaction of the amino acids with the surrounding aqueous environment in or outside the cell. Cunningham, et al., Science 244: 1081–1085 (1989). Those domains demonstrating functional sensitivity to the substitutions then are refined by introducing further or other variants at or for the sites of substitution.

Obviously, such variations that, for example, convert the amino acid sequence set forth in FIG. 2 (SEQ ID NO: 4) to the amino acid sequence of a known neurotrophic factor, such as NGF, BDNF, NT-3, NT-4/5, or another known polypeptide or protein are not included within the scope of this invention, nor are any other fragments, variants, and derivatives of the amino acid AL-1 that are not novel and unobvious over the prior art. Thus, while the site for introducing an amino acid sequence variation is predetermined, the nature of the mutation per se need not be predetermined. For example, to optimize the performance of a mutation at a given site, ala scanning or random mutagenesis is conducted at the target codon or region and the expressed AL-1 variants are screened for functional activity.

Amino acid sequence deletions generally range from about 1 to 30 residues, more preferably about 1 to 10 residues, and typically are contiguous. Deletions from regions of substantial homology with other tyrosine kinase receptor ligands, for example, are more likely to affect the functional activity of AL-1. Generally, the number of consecutive deletions will be selected so as to preserve the tertiary structure of AL-1 in the affected domain, e.g., beta-pleated sheet or alpha helix.

Amino acid sequence insertions include amino- and/or carboxyl-terminal fusions ranging in length from one amino acid residue to polypeptides containing a hundred or more residues, as well as intrasequence insertions of single or multiple amino acid residues. Intrasequence insertions (i.e., insertions made within the amino acid sequence set forth in FIG. 2, SEQ ID NO: 4) may range generally from about 1 to 10 residues, more preferably 1 to 5, most preferably 1 to 3. Examples of terminal insertions include AL-1 with an N-terminal methionyl residue (such as may result from the direct expression of AL-1 in recombinant cell culture), and AL-1 with a heterologous N-terminal signal sequence to improve the secretion of AL-1 from recombinant host cells. Such signal sequences generally will be homologous to the host cell used for expression of AL-1, and include STII or lpp for E. coli, alpha factor for yeast, and viral signals such as herpes gD for mammalian cells. Other insertions include the fusion to the N- or C-terminus of AL-1 of immunogenic polypeptides (for example, bacterial polypeptides such as beta-lactamase or an enzyme encoded by the E. coli trp locus, or yeast protein), and C-terminal fusions with proteins having a long half-life such as immunoglobulin constant regions, albumin, or ferritin, as described in PCT Pat. Pub. No. WO 89/02922 (published Apr. 6, 1989).

The third group of variants are those in which at least one amino acid residue in the amino acid sequence set forth in FIG. 2 (SEQ ID NO: 4), and preferably only one, has been removed and a different residue inserted in its place. The sites of greatest interest for making such substitutions are in the regions of the amino acid sequence set forth in FIG. 2 (SEQ ID NO: 4) that have the greatest homology with other tyrosine kinase receptor ligands. Those sites are likely to be important to the functional activity of the AL-1. Accordingly, to retain functional activity, those sites, especially those falling within a sequence of at least three other identically conserved sites, are substituted in a relatively conservative manner. Such conservative substitutions are shown in Table 1 under the heading of preferred substitutions. If such substitutions do not result in a change in functional activity, then more substantial changes, denominated exemplary substitutions in Table 1, or as further described below in reference to amino acid classes, may be introduced and the resulting variant AL-1 analyzed for functional activity.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Insertional, deletional, and substitutional changes in the amino acid sequence set forth in FIG. 2 (SEQ ID NO: 4) may be made to improve the stability of AL-1. For example, trypsin or other protease cleavage sites are identified by inspection of the encoded amino acid sequence for an arginyl or lysinyl residue. These are rendered inactive to protease by substituting the residue with another residue, preferably a basic residue such as glutamine or a hydrophobic residue such as serine; by deleting the residue; or by inserting a prolyl residue immediately after the residue. Also, any cysteine residues not involved in maintaining the proper conformation of AL-1 for functional activity may be substituted, generally with serine, to improve the oxidative stability of the molecule and prevent aberrant crosslinking.

Covalent modifications of AL-1 molecules also are included within the scope of this invention. For example, covalent modifications are introduced into AL-1 by reacting targeted amino acid residues of the AL-1 with an organic derivatizing agent that is capable of reacting with selected amino acid side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β- (5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are different alkyl groups, such as 1-cyclohexyl-3- (2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking AL-1 to a water-insoluble support matrix or surface for use in the method for purifying anti-AL-1 antibodies, or for therapeutic use. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)-dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains, acetylation of the N-terminal amine, and amidation of any C-terminal carboxyl group. Creighton, *Proteins: Structure and Molecular Properties*, pp. 79–86 (W.H. Freeman & Co., 1983). AL-1 also is covalently linked to nonproteinaceous polymers, e.g. polyethylene glycol, polypropylene glycol or polyoxyalkylenes, in the manner set forth in U.S. Pat. Nos. 4,179,337; 4,301,144; 4,496,689; 4,640,835; 4,670,417; or 4,791,192.

"AL-1 antagonist" or "antagonist" refers to a substance that opposes or interferes with a functional activity of AL-1.

"Cell," "host cell," "cell line," and "cell culture" are used interchangeably and all such terms should be understood to include progeny. Thus, the words "transformants" and "transformed cells" include the primary subject cell and cultures derived therefrom without regard for the number of times the cultures have been passaged. It should also be understood that all progeny may not be precisely identical in DNA content, due to deliberate or inadvertent mutations.

"Plasmids" are DNA molecules that are capable of replicating within a host cell, either extrachromosomally or as part of the host cell chromosome(s), and are designated by a lower case "p" preceded and/or followed by capital letters and/or numbers. The starting plasmids herein are commercially available, are publicly available on an unrestricted basis, or can be constructed from such available plasmids as disclosed herein and/or in accordance with published procedures. In certain instances, as will be apparent to the ordinarily skilled artisan, other plasmids known in the art may be used interchangeably with plasmids described herein.

"Control sequences" refers to DNA sequences necessary for the expression of an operably linked nucleotide coding sequence in a particular host cell. The control sequences that are suitable for expression in prokaryotes, for example, include origins of replication, promoters, ribosome binding sites, and transcription termination sites. The control sequences that are suitable for expression in eukaryotes, for example, include origins of replication, promoters, ribosome binding sites, polyadenylation signals, and enhancers.

An "exogenous" element is one that is foreign to the host cell, or homologous to the host cell but in a position within the host cell in which the element is ordinarily not found.

"Digestion" of DNA refers to the catalytic cleavage of DNA with an enzyme that acts only at certain locations in the DNA. Such enzymes are called restriction enzymes or restriction endonucleases, and the sites within DNA where such enzymes cleave are called restriction sites. If there are multiple restriction sites within the DNA, digestion will produce two or more linearized DNA fragments (restriction fragments). The various restriction enzymes used herein are commercially available and their reaction conditions, cofactors, and other requirements as established by the enzyme manufacturers are used. Restriction enzymes commonly are designated by abbreviations composed of a capital letter followed by other letters representing the microorganism from which each restriction enzyme originally was obtained and then a number designating the particular enzyme. In general, about 1 μg of DNA is digested with about 1–2 units of enzyme in about 20 μl of buffer solution. Appropriate buffers and substrate amounts for particular restriction enzymes are specified by the manufacturer, and/or are well known in the art.

"Recovery" or "isolation" of a given fragment of DNA from a restriction digest typically is accomplished by separating the digestion products, which are referred to as "restriction fragments," on a polyacrylamide or agarose gel by electrophoresis, identifying the fragment of interest on the basis of its mobility relative to that of marker DNA fragments of known molecular weight, excising the portion of the gel that contains the desired fragment, and separating the DNA from the gel, for example by electroelution.

"Ligation" refers to the process of forming phosphodiester bonds between two double-stranded DNA fragments. Unless otherwise specified, ligation is accomplished using known buffers and conditions with 10 units of T4 DNA ligase per 0.5 μg of approximately equimolar amounts of the DNA fragments to be ligated.

"Oligonucleotides" are short-length, single- or double-stranded polydeoxynucleotides that are chemically synthesized by known methods (involving, for example, triester, phosphoramidite, or phosphonate chemistry), such as described by Engels, et al., Agnew. Chem. Int. Ed. Engl. 28:716–734 (1989). They are then purified, for example, by polyacrylamide gel electrophoresis.

"Polymerase chain reaction," or "PCR," as used herein generally refers to a method for amplification of a desired nucleotide sequence in vitro, as described in U.S. Pat. No. 4,683,195. In general, the PCR method involves repeated cycles of primer extension synthesis, using two oligonucleotide primers capable of hybridizing preferentially to a template nucleic acid. Typically, the primers used in the PCR method will be complementary to nucleotide sequences within the template at both ends of or flanking the nucleotide sequence to be amplified, although primers complementary to the nucleotide sequence to be amplified also may be used. Wang, et al., in *PCR Protocols*, pp. 70–75 (Academic Press, 1990); Ochman, et al., in *PCR Protocols*, pp. 219–227; Triglia, et al., Nuc. Acids Res. 16:8186 (1988).

"PCR cloning" refers to the use of the PCR method to amplify a specific desired nucleotide sequence that is present amongst the nucleic acids from a suitable cell or tissue source, including total genomic DNA and cDNA transcribed from total cellular RNA. Frohman, et al., Proc. Nat. Acad. Sci. USA 85:8998–9002 (1988); Saiki, et al., Science 239: 487–492 (1988); Mullis, et al., Meth. Enzymol. 155:335–350 (1987).

"Stringent conditions" for hybridization or annealing of nucleic acid molecules are those that (1) employ low ionic strength and high temperature for washing, for example, 0.015 M NaCl/0.0015 M sodium citrate/0.1% sodium dodecyl sulfate (SDS) at 50° C., or (2) employ during hybridization a denaturing agent such as formamide, for example, 50% (vol/vol) formamide with 0.1% bovine serum albumin/ 0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/mL), 0.1% SDS, and 10% dextran sulfate at 42° C., with washes at 42° C. in 0.2×SSC and 0.1% SDS.

"AL-1 nucleic acid" is RNA or DNA that encodes AL-1. "AL-1 DNA" is DNA that encodes AL-1. AL-1 DNA is obtained from cDNA or genomic DNA libraries, or by in vitro synthesis. Identification of AL-1 DNA within a cDNA or a genomic DNA library, or in some other mixture of various DNAs, is conveniently accomplished by the use of an oligonucleotide hybridization probe that is labeled with a detectable moiety, such as a radioisotope. Keller, et al., *DNA Probes*, pp. 149–213 (Stockton Press, 1989). To identify DNA encoding AL-1, the nucleotide sequence of the hybridization probe preferably is selected so that the hybridization probe is capable of hybridizing preferentially to DNA encoding the AL-1 amino acid sequence set forth in FIG. 2 (SEQ ID NO: 4), or a variant or derivative thereof as described herein, under the hybridization conditions chosen. Another method for obtaining AL-1 nucleic acid is to chemically synthesize it using one of the methods described, for example, by Engels, et al., Agnew. Chem. Int. Ed. Engl. 28:716–734 (1989).

If the entire nucleotide coding sequence for AL-1 is not obtained in a single cDNA, genomic DNA, or other DNA, as determined, for example, by DNA sequencing or restriction endonuclease analysis, then appropriate DNA fragments (e.g., restriction fragments or PCR amplification products) may be recovered from several DNAs and covalently joined to one another to construct the entire coding sequence. The preferred means of covalently joining DNA fragments is by ligation using a DNA ligase enzyme, such as T4 DNA ligase.

"Isolated" AL-1 nucleic acid is AL-1 nucleic acid that is identified and separated from (or otherwise substantially free from), contaminant nucleic acid encoding other polypeptides. The isolated AL-1 nucleic acid can be incorporated into a plasmid or expression vector, or can be labeled for diagnostic and probe purposes, using a label as described further herein in the discussion of diagnostic assays and nucleic acid hybridization methods.

For example, isolated AL-1 DNA, or a fragment thereof comprising at least about 15 nucleotides, is used as a hybridization probe to detect, diagnose, or monitor disorders or diseases that involve changes in AL-1 expression, such as may result from neuron damage. In one embodiment of the invention, total RNA in a tissue sample from a patient (that is, a human or other mammal) can be assayed for the presence of AL-1 messenger RNA, wherein the decrease in the amount of AL-1 messenger RNA is indicative of neuronal degeneration.

Isolated AL-1 nucleic acid also is used to produce AL-1 by recombinant DNA and recombinant cell culture methods. In various embodiments of the invention, host cells are transformed or transfected with recombinant DNA molecules comprising an isolated AL-1 DNA, to obtain expression of the AL-1 DNA and thus the production of AL-1 in large quantities. DNA encoding amino acid sequence variants of AL-1 is prepared by a variety of methods known in the art. These methods include, but are not limited to, isolation from a natural source (in the case of naturally occurring amino acid sequence variants of AL-1) or preparation by site-directed (or oligonucleotide-mediated) mutagenesis, PCR mutagenesis, and cassette mutagenesis of an earlier prepared DNA encoding a variant or a non-variant form of AL-1.

Site-directed mutagenesis is a preferred method for preparing substitution, deletion, and insertion variants of AL-1 DNA. This technique is well known in the art, Zoller, et al., Meth. Enz. 100:4668–500 (1983); Zoller, et al., Meth. Enz.

154:329–350 (1987); Carter, Meth. Enz. 154:382–403 (1987); Horwitz, et al., Meth. Enz. 185:599–611 (1990), and has been used, for example, to produce amino acid sequence variants of trypsin and T4 lysozyme, which variants have certain desired functional properties. Perry, et al., Science 226:555–557 (1984); Craik, et al., Science 228:291–297 (1985).

Briefly, in carrying out site-directed mutagenesis of AL-1 DNA, the AL-1 DNA is altered by first hybridizing an oligonucleotide encoding the desired mutation to a single strand of such AL-1 DNA. After hybridization, a DNA polymerase is used to synthesize an entire second strand, using the hybridized oligonucleotide as a primer, and using the single strand of AL-1 DNA as a template. Thus, the oligonucleotide encoding the desired mutation is incorporated in the resulting double-stranded DNA.

Oligonucleotides for use as hybridization probes or primers may be prepared by any suitable method, such as by purification of a naturally occurring DNA or by in vitro synthesis. For example, oligonucleotides are readily synthesized using various techniques in organic chemistry, such as described by Narang, et al., Meth. Enzymol. 68:90–98 (1979); Brown, et al., Meth. Enzymol. 68:109–151 (1979); Caruther, et al., Meth. Enzymol. 154:287–313 (1985). The general approach to selecting a suitable hybridization probe or primer is well known. Keller, et al., DNA Probes, pp. 11–18 (Stockton Press, 1989). Typically, the hybridization probe or primer will contain 10–25 or more nucleotides, and will include at least 5 nucleotides on either side of the sequence encoding the desired mutation so as to ensure that the oligonucleotide will hybridize preferentially to the single-stranded DNA template molecule.

Multiple mutations are introduced into AL-1 DNA to produce amino acid sequence variants of AL-1 comprising several or a combination of insertions, deletions, or substitutions of amino acid residues as compared to the amino acid sequence set forth in FIG. 2 (SEQ ID NO: 4). If the sites to be mutated are located close together, the mutations may be introduced simultaneously using a single oligonucleotide that encodes all of the desired mutations. If, however, the sites to be mutated are located some distance from each other (separated by more than about ten nucleotides), it is more difficult to generate a single oligonucleotide that encodes all of the desired changes. Instead, one of two alternative methods may be employed.

In the first method, a separate oligonucleotide is generated for each desired mutation. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for introducing a single mutation: a single strand of a previously prepared AL-1 DNA is used as a template, an oligonucleotide encoding the first desired mutation is annealed to this template, and a heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid sequence variants of AL-1. Higuchi, in *PCR Protocols*, pp. 177–183 (Academic Press, 1990); Vallette, et al., Nuc. Acids Res. 17:723–733 (1989). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, for example, one of the primers is designed to overlap the position of the mutation and to contain the mutation; the sequence of the other primer must be identical to a nucleotide sequence within the opposite strand of the plasmid DNA, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone. Wagner, et al., in *PCR Topics*, pp. 69–71 (Springer-Verlag, 1991).

If the ratio of template to product amplified DNA is extremely low, the majority of product DNA fragments incorporate the desired mutation(s). This product DNA is used to replace the corresponding region in the plasmid that served as PCR template using standard recombinant DNA methods. Mutations at separate positions can be introduced simultaneously by either using a mutant second primer, or performing a second PCR with different mutant primers and ligating the two resulting PCR fragments simultaneously to the plasmid fragment in a three (or more)-part ligation.

Another method for preparing variants, cassette mutagenesis, is based on the technique described by Wells et al., Gene, 34:315–323 (1985). The starting material is the plasmid (or other vector) comprising the AL-1 DNA to be mutated. The codon(s) in the AL-1 DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the AL-1 DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated AL-1 DNA sequence.

AL-1 DNA, whether cDNA or genomic DNA or a product of in vitro synthesis, is ligated into a replicable vector for further cloning or for expression. "Vectors" are plasmids and other DNAs that are capable of replicating autonomously within a host cell, and as such, are useful for performing two functions in conjunction with compatible host cells (a vector-host system). One function is to facilitate the cloning of the nucleic acid that encodes the AL-1, i.e., to produce usable quantities of the nucleic acid. The other function is to direct the expression of AL-1. One or both of these functions are performed by the vector-host system. The vectors will contain different components depending upon the function they are to perform as well as the host cell with which they are to be used for cloning or expression.

To produce AL-1, an expression vector will contain nucleic acid that encodes AL-1 as described above. The AL-1 of this invention is expressed directly in recombinant cell culture, or as a fusion with a heterologous polypeptide, preferably a signal sequence or other polypeptide having a specific cleavage site at the junction between the heterologous polypeptide and the AL-1.

In one example of recombinant host cell expression, mammalian cells are transfected with an expression vector comprising AL-1 DNA and the AL-1 encoded thereby is recovered from the culture medium in which the recombinant host cells are grown. But the expression vectors and methods disclosed herein are suitable for use over a wide range of prokaryotic and eukaryotic organisms.

Prokaryotes may be used for the initial cloning of DNAs and the construction of the vectors useful in the invention. However, prokaryotes may also be used for expression of DNA encoding AL-1. Polypeptides that are produced in prokaryotic host cells typically will be non-glycosylated.

Plasmid or viral vectors containing replication origins and other control sequences that are derived from species compatible with the host cell are used in connection with prokaryotic host cells, for cloning or expression of an isolated DNA. For example, *E. coli* typically is transformed using pBR322, a plasmid derived from an *E. coli* species. Bolivar, et al., Gene 2:95–113 (1987). PBR322 contains genes for ampicillin and tetracycline resistance so that cells transformed by the plasmid can easily be identified or selected. For it to serve as an expression vector, the pBR322 plasmid, or other plasmid or viral vector, must also contain, or be modified to contain, a promoter that functions in the host cell to provide messenger RNA (mRNA) transcripts of a DNA inserted downstream of the promoter. Rangagwala, et al., Bio/Technology 9:477–479 (1991).

In addition to prokaryotes, eukaryotic microbes, such as yeast, may also be used as hosts for the cloning or expression of DNAs useful in the invention. *Saccharomyces cerevisiae*, or common baker's yeast, is the most commonly used eukaryotic microorganism. Plasmids useful for cloning or expression in yeast cells of a desired DNA are well known, as are various promoters that function in yeast cells to produce mRNA transcripts.

Furthermore, cells derived from multicellular organisms also may be used as hosts for the cloning or expression of DNAs useful in the invention. Mammalian cells are most commonly used, and the procedures for maintaining or propagating such cells in vitro, which procedures are commonly referred to as tissue culture, are well known. Kruse & Patterson, eds., *Tissue Culture* (Academic Press, 1977). Examples of useful mammalian cells are human cell lines such as 293, HeLa, and WI-38, monkey cell lines such as COS-7 and VERO, and hamster cell lines such as BHK-21 and CHO, all of which are publicly available from the American Type Culture Collection (ATCC), Rockville, Md. 20852 USA.

Expression vectors, unlike cloning vectors, should contain a promoter that is recognized by the host organism and is operably linked to the AL-1 nucleic acid. Promoters are untranslated sequences that are located upstream from the start codon of a gene and that control transcription of the gene (that is, the synthesis of mRNA). Promoters typically fall into two classes, inducible and constitutive. Inducible promoters are promoters that initiate high level transcription of the DNA under their control in response to some change in culture conditions, for example, the presence or absence of a nutrient or a change in temperature.

A large number of promoters are known, that may be operably linked to AL-1 DNA to achieve expression of AL-1 in a host cell. This is not to say that the promoter associated with naturally occurring AL-1 DNA is not usable. However, heterologous promoters generally will result in greater transcription and higher yields of expressed AL-1.

Promoters suitable for use with prokaryotic hosts include the β-lactamase and lactose promoters, Goeddel, et al., Nature 281:544–548 (1979), tryptophan (trp) promoter, Goeddel, et al., Nuc. Acids Res. 8:4057–4074 (1980), and hybrid promoters such as the tac promoter, deBoer, et al., Proc. Natl. Acad. Sci. USA 80:21–25 (1983). However, other known bacterial promoters are suitable. Their nucleotide sequences have been published, Siebenlist, et al., Cell 20:269–281 (1980), thereby enabling a skilled worker operably to ligate them to DNA encoding AL-1 using linkers or adaptors to supply any required restriction sites. Wu, et al., Meth. Enz. 152:343–349 (1987).

Suitable promoters for use with yeast hosts include the promoters for 3-phosphoglycerate kinase, Hitzeman, et al., J. Biol. Chem. 255:12073–12080 (1980); Kingsman, et al., Meth. Enz. 185:329–341 (1990), or other glycolytic enzymes such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase. Dodson, et al., Nuc. Acids res. 10:2625–2637 (1982); Emr, Meth. Enz. 185:231–279 (1990).

Expression vectors useful in mammalian cells typically include a promoter derived from a virus. For example, promoters derived from polyoma virus, adenovirus, cytomegalovirus (CMV), and simian virus 40 (SV40) are commonly used. Further, it is also possible, and often desirable, to utilize promoter or other control sequences associated with a naturally occurring DNA that encodes AL-1, provided that such control sequences are functional in the particular host cell used for recombinant DNA expression.

Other control sequences that are desirable in an expression vector in addition to a promoter are a ribosome binding site, and in the case of an expression vector used with eukaryotic host cells, an enhancer. Enhancers are cis-acting elements of DNA, usually about from 10–300 bp, that act on a promoter to increase the level of transcription. Many enhancer sequences are now known from mammalian genes (for example, the genes for globin, elastase, albumin, α-fetoprotein and insulin). Typically, however, the enhancer used will be one from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. Kriegler, Meth. Enz. 185:512–527 (1990).

Expression vectors may also contain sequences necessary for the termination of transcription and for stabilizing the messenger RNA (mRNA). Balbas, et al., Meth. Enz. 185: 14–37 (1990); Levinson, Meth. Enz. 185:485–511 (1990). In the case of expression vectors used with eukaryotic host cells, such transcription termination sequences may be obtained from the untranslated regions of eukaryotic or viral DNAs or cDNAs. These regions contain polyadenylation sites as well as transcription termination sites. Birnsteil, et al., Cell 41:349–359 (1985).

In general, control sequences are DNA sequences necessary for the expression of an operably liked coding sequence in a particular host cell. "Expression" refers to transcription and/or translation. "Operably linked" refers to the covalent joining of two or more DNA sequences, by means of enzymatic ligation or otherwise, in a configuration relative to one another such that the normal function of the sequences can be performed. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

Expression and cloning vectors also will contain a sequence that enables the vector to replicate in one or more selected host cells. Generally, in cloning vectors this sequence is one that enables the vector to replicate independently of the host chromosome(s), and includes origins of replication or autonomously replicating sequences. Such sequences are well known for a variety of bacteria, yeast, and viruses. The origin of replication from the plasmid pBR322 is suitable for most gram-negative bacteria, the 2μ plasmid origin is suitable for yeast, and various viral origins (for example, from SV40, polyoma, or adenovirus) are useful for cloning vectors in mammalian cells. Most expression vectors are "shuttle" vectors, i.e. they are capable of replication in at least one class of organisms but can be transfected into another organism for expression. For example, a vector may be cloned in *E. coli* and then the same vector is transfected into yeast or mammalian cells for expression even though it is not capable of replicating independently of the host cell chromosome.

The expression vector may also include an amplifiable gene, such as that comprising the coding sequence for dihydrofolate reductase (DHFR). Cells containing an expression vector that includes a DHFR gene may be cultured in the presence of methotrexate, a competitive antagonist of DHFR. This leads to the synthesis of multiple copies of the DHFR gene and, concomitantly, multiple copies of other DNA sequences comprising the expression vector, Ringold, et al., J. Mol. Apl. Genet. 1:165–175 (1981), such as a DNA sequence encoding AL-1. In that manner, the level of AL-1 produced by the cells may be increased.

DHFR protein encoded by the expression vector also may be used as a selectable marker of successful transfection. For example, if the host cell prior to transformation is lacking in DHFR activity, successful transformation by an expression vector comprising DNA sequences encoding AL-1 and DHFR protein can be determined by cell growth in medium containing methotrexate. Also, mammalian cells transformed by an expression vector comprising DNA sequences encoding AL-1, DHFR protein, and aminoglycoside 3' phosphotransferase (APH) can be determined by cell growth in medium containing an aminoglycoside antibiotic such as kanamycin or neomycin. Because eukaryotic cells do not normally express an endogenous APH activity, genes encoding APH protein, commonly referred to as neo$^r$ genes, may be used as dominant selectable markers in a wide range of eukaryotic host cells, by which cells transfected by the vector can easily be identified or selected. Jiminez, et al., Nature, 287:869–871 (1980); Colbere-Garapin, et al., J. Mol. Biol. 150:1–14 (1981); Okayama & Berg, Mol. Cell. Biol., 3:280–289 (1983).

Many other selectable markers are known that may be used for identifying and isolating recombinant host cells that express AL-1. For example, a suitable selection marker for use in yeast is the trp1 gene present in the yeast plasmid YRp7. Stinchcomb, et al., Nature 282:39–43 (1979); Kingsman, et al., Gene 7:141–152 (1979); Tschemper, et al., Gene 10:157–166 (1980). The trp1 gene provides a selection marker for a mutant strain of yeast lacking the ability to grow in tryptophan, for example, ATCC No. 44076 or PEP4-1 (available from the American Type Culture Collection, Rockville, Md. 20852 USA). Jones, Genetics 85:12 (1977). The presence of the trp1 lesion in the yeast host cell genome then provides an effective environment for detecting transformation by growth in the absence of tryptophan. Similarly, Leu2-deficient yeast strains (ATCC Nos. 20622 or 38626) are complemented by known plasmids bearing the Leu2 gene.

Particularly useful in the invention are expression vectors that provide for the transient expression in mammalian cells of DNA encoding AL-1. In general, transient expression involves the use of an expression vector that is able to efficiently replicate in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Yang, et al., Cell 47:3–10 (1986); Wong, et al., Science 228:810–815 (1985); Lee, et al., Proc. Nat Acad. Sci. USA 82:4360–4364 (1985). Thus, transient expression systems are particularly useful in the invention for expressing DNAs encoding amino acid sequence variants of AL-1, to identify those variants which are functionally active.

Since it is often difficult to predict in advance the characteristics of an amino acid sequence variant of AL-1, it will be appreciated that some screening of such variants will be needed to identify those that are functionally active. Such screening may be performed in vitro, using routine assays for receptor binding, or assays for axonal growth or development, or using immunoassays with monoclonal antibodies that selectively bind to AL-1 that is functionally active AL-1, such as a monoclonal antibody that selectively binds to the active site or receptor binding site of AL-1.

As used herein, the terms "transformation" and "transfection" refer to the process of introducing a desired nucleic acid, such a plasmid or an expression vector, into a host cell. Various methods of transformation and transfection are available, depending on the nature of the host cell. In the case of *E. coli* cells, the most common methods involve treating the cells with aqueous solutions of calcium chloride and other salts. In the case of mammalian cells, the most common methods are transfection mediated by either calcium phosphate or DEAE-dextran, or electroporation. Sambrook, et al., eds., *Molecular Cloning*, pp. 1.74–1.84 and 16.30–16.55 (Cold Spring Harbor Laboratory Press, 1989). Following transformation or transfection, the desired nucleic acid may integrate into the host cell genome, or may exist as an extrachromosomal element.

Host cells that are transformed or transfected with the above-described plasmids and expression vectors are cultured in conventional nutrient media modified as is appropriate for inducing promoters or selecting for drug resistance or some other selectable marker or phenotype. The culture conditions, such as temperature, pH, and the like, suitably are those previously used for culturing the host cell used for cloning or expression, as the case may be, and will be apparent those skilled in the art.

Suitable host cells for cloning or expressing the vectors herein are prokaryotes, yeasts, and higher eukaryotes, including insect, vertebrate, and mammalian host cells. Suitable prokaryotes include eubacteria, such as Gram-negative or Gram-positive organisms, for example, *E. coli*, *Bacillus* species such as *B. subtilis*, *Pseudomonas* species such as *P. aeruginosa*, *Salmonella typhimurium*, or *Serratia marcescans*.

In addition to prokaryotes, eukaryotic microbes such as filamentous fungi or yeast are suitable hosts for AL-1-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*, Beach and Nurse, Nature 290:140–142 (1981), *Pichia pastoris*, Cregg, et al., Bio/Technology 5:479–485 (1987); Sreekrishna, et al., Biochemistry 28:4117–4125 (1989), *Neurospora crassa*, Case, et al., Proc. Natl. Acad. Sci. USA 76:5259–5263 (1979), and *Aspergillus* hosts such as *A. nidulans*, Ballance, et al., Biochem. Biophys. Res. Commun. 112:284–289 (1983); Tilburn, et al., Gene 26:205–221 (1983); Yelton, et al., Proc. Natl. Acad. Sci. USA 81:1470–1474 (1984), and *A. nicer*, Kelly, et al., EMBO J. 4:475–479 (1985).

Suitable host cells for the expression of AL-1 also are derived from multicellular organisms. Such host cells are capable of complex processing and glycosylation activities. In principle, any higher eukaryotic cell culture is useable, whether from vertebrate or invertebrate culture. It will be appreciated, however, that because of the species-, tissue-, and cell-specificity of glycosylation, Rademacher, et al., Ann. Rev. Biochem. 57:785–838 (1988), the extent or pattern of glycosylation of AL-1 in a foreign host cell typically will differ from that of AL-1 obtained from a cell in which it is naturally expressed.

Examples of invertebrate cells include insect and plant cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified. Luckow, et al., Bio/Technology 6:47–55 (1988); Miller, et al., in *Genetic Engineering*, vol. 8, pp. 277–279 (Plenum Publishing, 1986); Maeda, et al., Nature 315:592–594 (1985).

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously altered to contain AL-1 DNA. During incubation of the plant cells with *A. tumefaciens*, the DNA encoding the AL-1 is transferred into cells, such that they become transfected, and will, under appropriate conditions, express the AL-1 DNA. In addition, regulatory and signal sequences compatible with plant cells are available, such as the nopaline synthase promoter and polyadenylation signal sequences, and the ribulose biphosphate carboxylase promoter. Depicker, et al., J. Mol. Appl. Gen. 1:561–573 (1982). Herrera-Estrella, et al., Nature 310:115–120 (1984). In addition, DNA segments isolated from the upstream region of the T-DNA 780 gene are capable of activating or increasing transcription levels of plant-expressible genes in recombinant DNA-containing plant tissue. European Pat. Pub. No. EP 321,196 (published Jun. 21, 1989).

However, interest has been greatest in vertebrate cells, and propagation of vertebrate cells in culture (tissue culture) has become a routine procedure in recent years. Kruse & Patterson, eds., *Tissue Culture* (Academic Press, 1973). Examples of useful mammalian host cells are the monkey kidney CV1 line transformed by SV40 (COS-7, ATCC CRL 1651); human embryonic kidney line 293 (or 293 cells subcloned for growth in suspension culture), Graham, et al., J. Gen Virol. 36:59–72 (1977); baby hamster kidney cells (BHK, ATCC CCL 10); Chinese hamster ovary cells (including DHFR-deficient CHO cells, Urlaub, et al., Proc. Natl. Acad. Sci. USA 77:4216–4220 (1980); mouse sertoli cells (TM4, Mather, Biol. Reprod. 23:243–251 (1980); monkey kidney cells (CV1, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather, et al., Annals N.Y. Acad. Sci. 383:44–68 (1982)); MRC 5 cells; FS4 cells; and a human hepatoma line (Hep G2).

Construction of suitable vectors containing the nucleotide sequence encoding AL-1 and appropriate control sequences employs standard recombinant DNA methods. DNA is cleaved into fragments, tailored, and ligated together in the form desired to generate the vectors required.

For analysis to confirm correct sequences in the vectors constructed, the vectors are analyzed by restriction digestion (to confirm the presence in the vector of predicted restriction endonuclease) and/or by sequencing by the dideoxy chain termination method of Sanger, et al., Proc. Nat. Acad. Sci. USA 72:3918–3921 (1979).

The mammalian host cells used to produce the AL-1 of this invention may be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham, et al., Meth. Enz. 58:44–93 (1979); Barnes, et al., Anal. Biochem. 102: 255–270 (1980); Bottenstein, et al., Meth. Enz. 58:94–109 (1979); U.S. Pat. No. 4,560,655; 4,657,866; 4,767,704; or 4,927,762; or in PCT Pat. Pub. Nos. WO 90/03430 (published Apr. 5, 1990), may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in culture in vitro as well as cells that are within a host animal, for example, as a result of transplantation or implantation.

It is further contemplated that the AL-1 of this invention may be produced by homologous recombination, for example, as described in PCT Pat. Pub. No. WO 91/06667 (published May 16, 1991). Briefly, this method involves transforming cells containing an endogenous gene encoding AL-1 with a homologous DNA, which homologous DNA comprises (1) an amplifiable gene, such as DHFR, and (2) at least one flanking sequence, having a length of at least about 150 base pairs, which is homologous with a nucleotide sequence in the cell genome that is within or in proximity to the gene encoding AL-1. The transformation is carried out under conditions such that the homologous DNA integrates into the cell genome by recombination. Cells having integrated the homologous DNA then are subjected to conditions which select for amplification of the amplifiable gene, whereby the AL-1 gene amplified concomitantly. The resulting cells then are screened for production of desired amounts of AL-1. Flanking sequences that are in proximity to a gene encoding AL-1 are readily identified, for example, by the method of genomic walking, using as a starting point the AL-1 nucleotide sequence set forth in FIG. 2 (SEQ ID NO: 3). Spoerel, et al., Meth. Enz. 152:598–603 (1987).

Gene amplification and/or gene expression may be measured in a sample directly, for example, by conventional Southern blotting to quantitate DNA, or Northern blotting to quantitate mRNA, using an appropriately labeled oligonucleotide hybridization probe, based on the sequences provided herein. Various labels may be employed, most commonly radioisotopes, particularly $^{32}$P. However, other techniques may also be employed, such as using biotin-modified nucleotides for introduction into a polynucleotide. The biotin then serves as the site for binding to avidin or antibodies, which may be labeled with a wide variety of labels, such as radioisotopes, fluorophores, chromophores, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of the gene product, AL-1. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu, et al., Am. J. Clin. Path., 75:734–738 (1980). Antibodies useful for immunohistochemical staining and/or assay of sample fluids may be either monoclonal or polyclonal. Conveniently, the antibodies may be prepared against a synthetic peptide based on the DNA sequences provided herein.

AL-1 preferably is recovered from the culture medium as a secreted polypeptide, although it also may be recovered from host cell lysates. To obtain AL-1 that is substantially free of contaminating proteins or polypeptides of the host cell in which it is produced it is necessary to purify the AL-1, based on the differential physical properties of AL-1 as compared to the contaminants with which it may be associated. For example, as a first step, the culture medium or lysate is centrifuged to remove particulate cell debris. AL-1 thereafter is purified from contaminant soluble proteins and polypeptides, for example, by ammonium sulfate or ethanol precipitation, gel filtration (molecular exclusion chromatography), ion-exchange chromatography, immunoaffinity chromatography, reverse phase HPLC, and/or gel electrophoresis. For example, AL-1 can be purified by immunoaffinity chromatography using a REK7-IgG resin (comprising REK7-IgG coupled to the resin material), as described in Example 5.

Amino acid sequence variants and derivatives of AL-1 are recovered in the same fashion, taking account of any distinguishing features or physical properties of the particular AL-1. For example, in the case of a fusion protein comprising AL-1 and another protein or polypeptide, such as a bacterial or viral antigen, a significant degree of purification may be obtained by using an immunoaffinity column containing antibody to the antigen. In any event, the ordinarily skilled artisan will appreciate that purification methods suitable for naturally occurring AL-1 may require modification to account for changes in the character of AL-1 or its variants or derivatives produced in recombinant host cells.

The purity of AL-1 produced according to the present invention is determined according to methods well known in the art, such as by analytical sodium dodecyl sulfate (SDS) gel electrophoresis, immunoassay, or amino acid composition or sequence analysis electrophoresis. Preferably, the AL-1 is purified to such an extent that it is substantially free of other proteins. For therapeutic uses, the purified AL-1 will be greater than 99% AL-1 and, accordingly, non-AL-1 proteins will comprise less than 1% of the total protein in the purified AL-1 composition.

AL-1 may be used as an immunogen to generate anti-AL-1 antibodies. Such antibodies, which specifically bind to AL-1, are useful as standards in assays for AL-1, such as by labeling purified AL-1 for use as a standard in a radioimmunoassay, enzyme-linked immunoassay, or competitive-type receptor binding assays radioreceptor assay, as well as in affinity purification techniques. Ordinarily, the anti-AL-1 antibody will bind AL-1 with an affinity of at least about $10^6$ L/mole, and preferably at least about $10^7$ L/mole.

Polyclonal antibodies directed toward AL-1 generally are raised in animals by multiple subcutaneous or intraperitoneal injections of AL-1 and an adjuvant. It may be useful to conjugate AL-1 or a peptide fragment thereof to a carrier protein that is immunogenic in the species to be immunized, such as keyhole limpet hemocyanin, serum albumin, bovine thyroglobulin, or soybean trypsin inhibitor, using a bifunctional or derivatizing agent, for example, maleimidobenzoyl sulfosuccinimide ester (conjugation through cysteine residues), N-hydroxysuccinimide (conjugation through lysine residues), glutaraldehyde, succinic anhydride, $SOCl_2$, or $R^1N=C=NR$, where R and $R^1$ are different alkyl groups.

Animals are immunized with such AL-1-carrier protein conjugates combining 1 mg or 1 μg of conjugate (for rabbits or mice, respectively) with 3 volumes of Freund's complete adjuvant and injecting the solution intradermally at multiple sites. One month later the animals are boosted with ⅕th to ⅒th the original amount of conjugate in Freund's complete adjuvant by subcutaneous injection at multiple sites. 7 to 14 days later animals are bled and the serum is assayed for anti-AL-1 antibody titer. Animals are boosted until the antibody titer plateaus. Preferably, the animal is boosted by injection with a conjugate of the same AL-1 with a different carrier protein and/or through a different cross-linking agent. Conjugates of AL-1 and a suitable carrier protein also can be made in recombinant cell culture as fusion proteins. Also, aggregating agents such as alum are used to enhance the immune response.

Monoclonal antibodies directed toward AL-1 are produced using any method which provides for the production of antibody molecules by continuous cell lines in culture. The modifier "monoclonal" indicates the character of the antibody as being obtained from a substantially homogeneous population of antibodies, and is not to be construed as requiring production of the antibody by any particular method. Examples of suitable methods for preparing monoclonal antibodies include the original hybridoma method of Kohler, et al., Nature 256:495–497 (1975), and the human B-cell hybridoma method, Kozbor, J. Immunol. 133:3001 (1984); Brodeur, et al., *Monoclonal Antibody Production Techniques and Applications*, pp. 51–63 (Marcel Dekker, Inc., New York, 1987).

The monoclonal antibodies of the invention specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly, et al., U.S. Pat. No. 4,816,567; Morrison, et al., Proc. Natl. Acad. Sci. 81:6851–6855 (1984)).

In a preferred embodiment, the chimeric anti-AL-1 antibody is a "humanized" antibody. Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain.

Humanization can be performed following methods known in the art (Jones, et al., Nature 321:522–525 (1986); Riechmann, et al., Nature, 332:323–327 (1988); Verhoeyen, et al., Science 239:1534–1536 (1988)), by substituting rodent complementarity-determining regions (CDRs) for the corresponding regions of a human antibody. Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, for example, Jakobovits, et al., Proc. Natl. Acad. Sci. 90: 2551–2555 (1993); Jakobovits, et al., Nature 362:255–258 (1993); Bruggermann, et al., Year in Immuno. 7:33 (1993). Human antibodies can also be produced in phage-display libraries (Hoogenboom, et al., J. Mol. Biol. 227:381 (1991); Marks, et al., J. Mol. Biol. 222:581 (1991).

For diagnostic applications, anti-AL-1 antibodies typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; radioactive isotopic labels, such as, e.g., $^{125}I$, $^{32}P$, $^{14}C$, or $^3H$, or an enzyme, such as alkaline phosphatase, beta-galactosidase or horseradish peroxidase.

Any method known in the art for separately conjugating the antibody to the detectable moiety may be employed, including those methods described by David, et al., Biochemistry 13:1014–1021 (1974); Pain, et al., J. Immunol. Meth. 40:219–231 (1981); and Bayer, et al., Meth. Enz. 184:138–163 (1990).

The anti-AL-1 antibodies may be employed in any known assay method, such as competitive binding assays, direct and indirect sandwich assays, and immunoprecipitation assays. Zola, *Monoclonal Antibodies: A Manual of Techniques*, pp. 147–158 (CRC Press, Inc., 1987).

Competitive binding assays rely on the ability of a labeled standard (e.g., AL-1 or an immunologically reactive portion thereof) to compete with the test sample analyte (AL-1) for binding with a limited amount of antibody. The amount of AL-1 in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David, et al., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

The anti-AL-1 antibodies of the invention also are useful for in vivo imaging, wherein an antibody labeled with a detectable moiety is administered to a host, preferably into the bloodstream, and the presence and location of the labeled antibody in the host is assayed. This imaging technique is useful in the staging and treatment of various neurological disorders. The antibody may be labeled with any moiety that is detectable in a host, whether by nuclear magnetic resonance, radiology, or other detection means known in the art.

Neutralizing anti-AL-1 antibodies are useful as antagonists of AL-1. The term "neutralizing anti-AL-1 antibody" as used herein refers to an antibody that is capable of specifically binding to AL-1, and which is capable of substantially inhibiting or eliminating the functional activity of AL-1 in vivo or in vitro. Typically a neutralizing antibody will inhibit the functional activity of AL-1 at least about 50%, and preferably greater than 80%, as determined, for example, by an in vitro receptor binding assay, or in vitro axon bundling assay, such as described in Example 8.

Other AL-1 antagonists are prepared using AL-1 receptor proteins, such as REK7. One example of an AL-1 antagonist is the REK7-IgG chimeric protein described herein. Another example of an AL-1 antagonist is a soluble form of an AL-1 receptor, which comprises the extracellular domain or the receptor substantially free of the transmembrane domain.

The soluble form of the receptor can be used directly as an antagonist, or the receptor can be used to screen for small molecules that would antagonize AL-1 activity.

AL-1 is believed to be useful in promoting the development, maintenance, or regeneration of neurons in vivo, including central (brain and spinal chord), peripheral (sympathetic, prasympathetic, sensory, and enteric neurons), and motorneurons. Accordingly, AL-1 may be utilized in methods for the diagnosis and/or treatment of a variety of neurologic diseases and disorders.

In various embodiments of the invention, purified AL-1 can be administered to patients in whom the nervous system has been damaged by trauma, surgery, stroke, ischemia, infection, metabolic disease, nutritional deficiency, malignancy, or toxic agents, to promote the survival or growth of neurons. For example, AL-1 can be used to promote the survival or growth of motorneurons that are damaged by trauma or surgery. Also, AL-1 can be used to treat motorneuron disorders, such as amyotrophic lateral sclerosis (Lou Gehrig's disease), Bell's palsy, and various conditions involving spinal muscular atrophy, or paralysis. AL-1 can be used to treat human neurodegenerative disorders, such as Alzheimer's disease, Parkinson's disease, epilepsy, multiple sclerosis, Huntington's chorea, Down's Syndrome, nerve deafness, and Meniere's disease.

Further, AL-1 can be used to treat neuropathy, and especially peripheral neuropathy. "Peripheral neuropathy" refers to a disorder affecting the peripheral nervous system, most often manifested as one or a combination of motor, sensory, sensorimotor, or autonomic neural dysfunction. The wide variety of morphologies exhibited by peripheral neuropathies can each be attributed uniquely to an equally wide number of causes. For example, peripheral neuropathies can be genetically acquired, can result from a systemic disease, or can be induced by a toxic agent. Examples include but are not limited to distal sensorimotor neuropathy, or autonomic neuropathies such as reduced motility of the gastrointestinal tract or atony of the urinary bladder. Examples of neuropathies associated with systemic disease include post-polio syndrome; examples of hereditary neuropathies include Charcot-Marie-Tooth disease, Refsum's disease, Abetalipoproteinemia, Tangier disease, Krabbe's disease, Metachromatic leukodystrophy, Fabry's disease, and Dejerine-Sottas syndrome; and examples of neuropathies caused by a toxic agent include those caused by treatment with a chemotherapeutic agent such as vincristine, cisplatin, methotrexate, or 3'-azido-3'-deoxythymidine.

In still further embodiments of the invention, AL-1 antagonists, and especially anti-AL-1 antibodies, can be administered to patients suffering from neurologic diseases and disorders characterized by excessive production of AL-1. AL-1 antagonists can be used in the prevention of aberrant regeneration of sensory neurons such as may occur post-operatively, or in the selective ablation of sensory neurons, for example, in the treatment of chronic pain syndromes.

Therapeutic formulations of AL-1 and AL-1 antagonists for treating neurologic diseases and disorders are prepared by mixing AL-1 or anti-AL-1 antibody, having the desired degree of purity, with optional physiologically acceptable carriers, excipients, or stabilizers which are well known. Acceptable carriers, excipients or stabilizers are nontoxic at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

It may be desirable to adsorb AL-1 onto a membrane, such as a silastic membrane, which can be implanted in proximity to damaged neural tissue, or to incorporate AL-1 into liposomes. PCT Pat. Pub. No. WO 91/04014 (published Apr. 4, 1991). In another embodiment, the AL-1 used for therapeutic effect is AL-1 covalently joined to another protein, such as an immunoglobulin domain (for example, to produce an AL1-IgG fusion protein).

AL-1 optionally is combined with or administered in concert with other neurotrophic factors to achieve a desired therapeutic effect. For example, AL-1 may be used together with NGF, NT-3, BDNF, NT-4/5, an insulin-like growth factor (e.g., IGF-1, IGF-2, or IGF-3) or another neurotrophic factor to achieve a synergistic stimulatory effect on the growth of sensory neurons, wherein the term "synergistic" means that the effect of the combination of AL-1 with a second substance is greater than that achieved with either substance used individually.

AL-1 and AL-1 antagonists to be used for in vivo administration must be sterile. This is readily accomplished by filtration of a solution of AL-1 or anti-AL-1 antibody through sterile filtration membranes. Thereafter, the filtered solution may be placed into a container having a sterile access port, for example, an intravenous solution bag or vial having a stopper pierceable by a hypodermic injection needle. The filtered solution also may be lyophilized to produce sterile AL-1 or anti-AL-1 antibody in a powder form.

Methods for administering AL-1 and AL-1 antagonists in vivo include injection or infusion by intravenous, intraperitoneal, intracerebral, intrathecal, intramuscular, intraocular, intraarterial, or intralesional routes, and by means of sustained-release formulations.

Sustained-release formulations generally consist of AL-1 or AL-1 antagonists and a matrix from which the AL-1 or AL-1 antagonists are released over some period of time. Suitable matrices include semipermeable polymer matrices in the form of shaped articles, for example, membranes, fibers, or microcapsules. Sustained release matrices may comprise polyesters, hydrogels, polylactides, U.S. Pat. No. 3,773,919, copolymers of L-glutamic acid and gamma ethyl-L-glutamate, Sidman, et al., Biopolymers, 22: 547–556 (1983), poly (2-hydroxyethyl-methacrylate), or ethylene vinyl acetate, Langer, et al., J. Biomed. Mater. Res. 15: 167–277 (1981); Langer, Chem. Tech. 12:98–105 (1982).

In one embodiment of the invention, the therapeutic formulation comprises AL-1 or AL-1 antagonist entrapped within or complexed with liposomes. For example, AL-1 covalently joined to a glycophosphatidyl-inositol moiety may be used to form a liposome comprising AL-1. In a further embodiment, the therapeutic formulation comprises cells actively producing AL-1 or AL-1 antagonist. Such cells may be directly introduced into the tissue of a patient, or may be encapsulated within porous membranes which are then implanted in a patient, in either case providing for the delivery of AL-1 or anti-AL-1 antagonist into areas within the body of the patient in need of increased or decreased concentrations of AL-1. Alternatively, an expression vector comprising AL-1 DNA may be used for in vivo transformation of a patient's cells to accomplish the same result.

An effective amount of AL-1 or anti-AL-1 antibody to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 µg/kg to up to 100 mg/kg or more, depending on the factors mentioned above. Where possible, it is desirable to determine appropriate dosage ranges first in vitro, for example, using assays for neuronal cell survival or growth which are known in the art, and then in suitable animal models, from which dosage ranges for human patients may be extrapolated. In a specific embodiment of the invention, a pharmaceutical composition effective in promoting the survival or growth of neurons will provide a local GPA concentration in vivo of between about 0.1 and 10 ng/ml.

In summary, by providing nucleic acid molecules encoding AL-1, the present invention enables for the first time the production of AL-1 by recombinant DNA methods, thus providing a reliable source of sufficient quantities of AL-1 for use in various diagnostic and therapeutic applications. In view of its distinct biological properties, purified recombinant AL-1 will be especially useful in a variety of circumstances where it is necessary or desirable to assure neuronal growth and survival, but where other neurotrophic factors either cannot be used or are ineffective.

The following examples are offered by way of illustration only and are not intended to limit the invention in any manner. All patent and literature references cited herein are expressly incorporated.

EXAMPLE 1

Identification and Isolation of REK7 cDNA

To isolate novel growth factors that might act on central nervous system neurons, a search for new tyrosine kinase receptors was made using a polymerase chain reaction (PCR). Degenerate sense and antisense primers were prepared that corresponded to conserved amino acid sequences within the kinase domain of many receptor tyrosine kinases. The nucleotide sequences of the primers were as follows:

```
                                       (SEQ. ID. NO. 5)
5' - CCCTCGAGGTCGACCAYMGIGAYYTIGCIRCIMGIAA - 3'

(SEQ. ID. NO. 6)
5' - CCCTCGAGGTCGACCAYMGIGAYYTIGCITGYMGIAA - 3'

(SEQ. ID. NO. 7)
5' - CCGCGGTGCGGCCGCCRWAISHCCAIACRTC - 3'
```

Figure 1A:
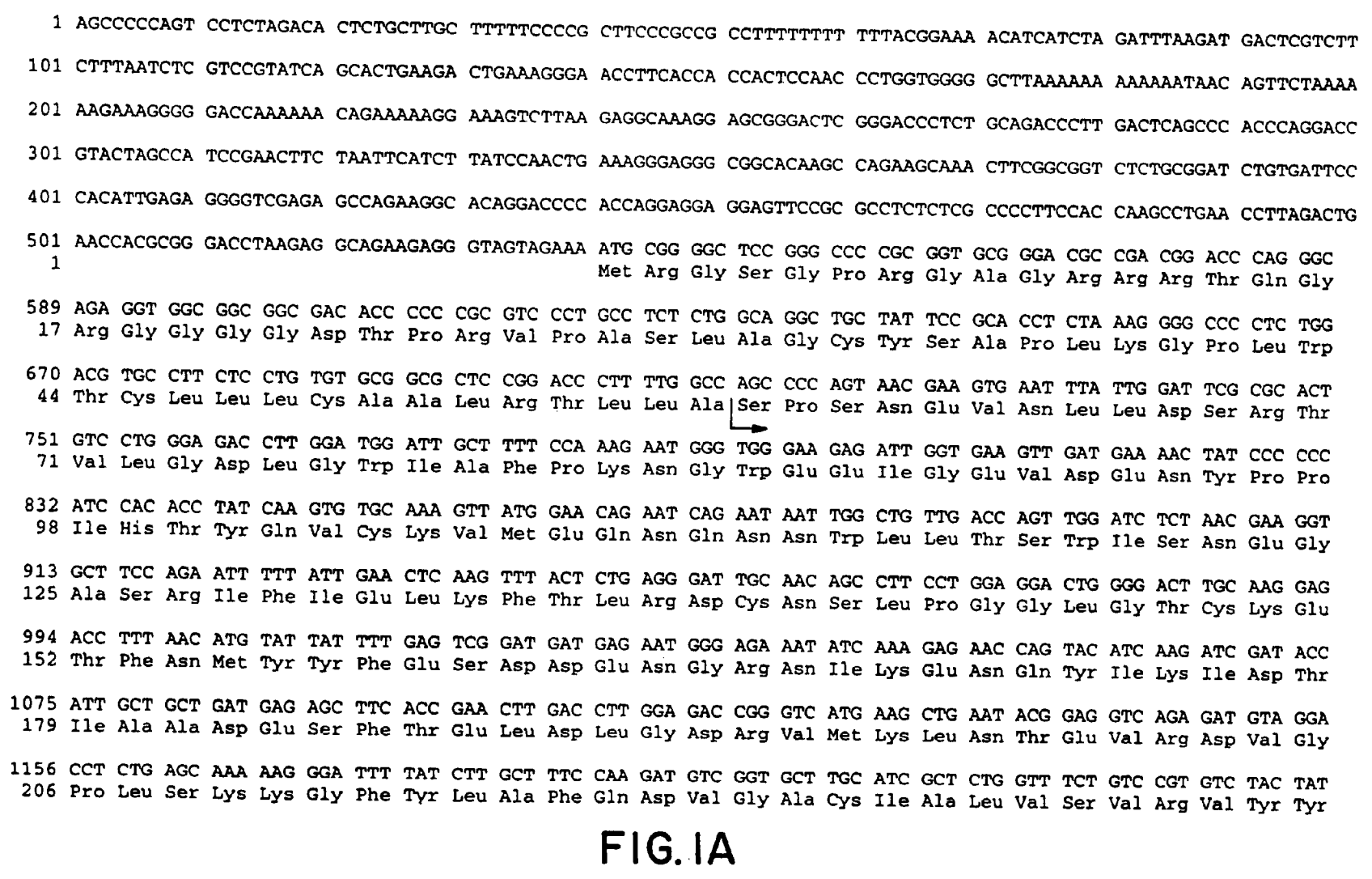

These degenerate primers were used to amplify the cDNAs of an adult mouse hippocampal cDNA library using standard PCR methods, and the resulting amplified cDNAs were subcloned and sequenced. One of these cDNAs, approximately 200 bp in size, encoded a deduced amino acid sequence within the kinase domains of the eph family of receptor tyrosine kinases. This 200 bp cDNA then was used as a probe to isolate a full-length cDNA from a rat hippocampal cDNA library. FIGS. 1A–D show the nucleotide sequence (SEQ. ID NO. 1) of the full-length cDNA, and the deduced amino acid sequence (SEQ. ID NO. 2) of the encoded protein, termed REK7.

REK7 appears to be the rat homologue of cek7, and is closely related to ehk-1 and bsk. (Maisonpierre, et al., Oncogene 8:3277–3288 (1993); Zhou, et al., J. Neurosci. Res. 37:129–143 (1994)). In particular, the REK7 cDNA corresponds to a splice variant of ehk-1 lacking the first of two tandem fibronectin type-III domains.

EXAMPLE 2

Construction of REK7 Expression Plasmid

A cDNA encoding REK7 was cloned into the mammalian expression vector pRK7 (PCT Publication No. WO 90/02798, published Sep. 22, 1990), between the XbaI and BamHI restriction endonuclease cleavage sites of pRK7, to produce the expression plasmid pRK-REK7.

EXAMPLE 3

Production of REK7-IgG Fusion Protein

DNA encoding a soluble REK7-IgG chimera was constructed by joining DNAs encoding the extracellular domain of REK7 and the $F_c$ domain of the $IgG_1$ heavy chain. The DNA sequence encoding the $IgG_1$ portion of the REK7-IgG chimera was obtained from the CD4-IgG expression plasmid pRKCD4$_2$F$_{cI}$ (Capon, et al., Nature 337:525 (1989); Byrn, et al., Nature 344:667 (1990)). That plasmid encodes a hybrid polypeptide consisting of residues 1–180 of the mature human CD4 protein (two N-terminal CD4 variable domains) fused to the portion of the human immunoglobulin $IgG_1$ protein extending from the aspartic acid residue at position 216 (which is the first residue of the $IgG_1$ hinge after the cysteine residue involved in heavy-light chain bonding) to amino acid residue 441 (the numbering of residues in $IgG_1$ is based on amino acid residue 114 being the first residue of the heavy chain constant region (Kabat, et al., Sequences of Proteins of Immunological Interest, 4th ed. (1987)).

PCR was used to generate a 600 bp fragment containing sequences encoding the 3'-end of the REK7 extracellular domain (terminating at Gln$_{462}$, the junction between the extracellular domain and the transmembrane domain), joined to sequences encoding the 5'-end of a human $IgG_1$ Fc domain. The 600 bp fragment was constructed in three steps. First, a DNA fragment containing the 3'-end of the REK7 extracellular domain was amplified using pRK/EK7 as template and 5'-TCTGTGACAGACGATCCTCCC (primer 1, SEQ. ID. NO. 8) and 5'-GCACGGTGGACATGT-TGAGTTTTGTCCTGGCTTTGATCATTA-GATGCTGCAAC as primers. Second, a DNA fragment containing the 5'-end of a human $IgG_1$ Fc domain was amplified using pRKCD4-IgG as template and 5'-GTTGCAGCATCTAATGAT-CAAAGCCAGGACAAAACTCACACATGTC-CACCGTGC (SEQ. ID. NO. 10) and 5'GCACTTGTACTCCTTGCC (primer 2, SEQ. ID. NO. 11) as primers. Finally, the two resulting amplified DNA fragments were mixed together and covalently joined in a third PCR using primers 1 and 2, to produce a 600 bp DNA fragment encoding a REK7-IgG fusion protein.

Since the REK7 cDNA appears to contain sequences that promote rearrangements and deletions during DNA manipulation, assembly of an expression plasmid encoding the full-length REK7-IgG protein was carried out in three steps. First, the 600 bp PCR product (see above) was cut by digestion with KpnI and SacII restriction endonucleases and the resulting KPNI-SacII fragment was gel purified. pRKCD4-IgG$_1$ was cleaved with HindIII and SacII restriction endonucleases and a 502 bp fragment was isolated. These KpnI-SacII fragment and the 502 bp fragment were ligated into a Bluescript vector (Stratagene, La Jolla, Calif. USA) cleaved with KpnI and HindIII, to produce REK7-IgG Intermediate 1.

Second, REK-IgG Intermediate 1 was cut with KpnI and EcoRI restriction endonucleases and the resulting 1000 bp fragment was isolated. pRK-REK7 was cut with KpnI and ApaI restriction endonucleases and a 786 bp fragment was isolated. The 1000 bp fragment and the 786 bp fragment were ligated into a Bluescript vector cut with ApaI and EcoRI, to produce REK7-IgG Intermediate 2.

Finally, the complete pRKREK-IgG expression plasmid (7004 bp) was assembled by ligation of the three fragments as follows. REK7-IgG Intermediate 2 was cut with PflMI and EcoRI restriction endonucleases and a 1860 bp fragment was isolated. pRK-REK7 was cut with PflMI and PstI restriction endonucleases and a 512 bp fragment was isolated. These two fragments were ligated to the pRK7 vector cut with PstI and EcoRI, to produce pRKREK7-IgG.

REK7-IgG was expressed in human embryonic kidney 293 cells [Graham, et al., *J. Gen. Virol.* 36, 59 (1977) and Chinese hamster ovary (CHO) cells by transient transfection using the calcium phosphate precipitation method as described by Capon, et al., supra, and Byrn, et al., supra. The REK7-IgG chimera was purified to greater than 95% homogeneity from serum free cell culture supernatants by affinity chromatography on immobilized *Staphylococcus aureus* Protein A as described by Capon, et al., supra.]

EXAMPLE 4

Identification of a Source for REK7 Ligand

In an effort to identify the putative REK7 ligand, REK7-IgG was used to screen cultured cell lines for cell surface expression of REK7-binding activity. Cell lines were assayed by incubation with REK7-IgG and fluorescent anti-IgG antibody followed by fluorescence-activated cell sorting (FACS).

For example, human breast carcinoma cell line BT20 (American type Culture Collection, Rockville, Md., USA) was grown in 50/50 (v/v) F12/DMEM low glucose medium, with 10% fetal calf serum (FCS) and 1 mM glutamine (collectively, growth medium), in a 5% $CO_2$. Cells at 80–90% confluence were harvested with 5 mM EDTA in phosphate buffered saline (PBS), counted and resuspended in binding buffer (50/50 (v/v) F12/DMEM low glucose medium, 5% FCS, and 1 mg/ml bovine serum albumin (BSA)) at a cell density of $5 \times 10^6$ cells/ml. To 1 ml of cells, 1 µg of REK7-IgG was added and incubated for 2 hours at room temperature. The cells then were collected by centrifugation, incubated with a fluorescein-labelled anti-human IgG1-Fc for 1 hour at room temperature, then analyzed by FACS.

The BT20 cell line and the human cervical carcinoma cell line HeLa (American type Culture Collection, Rockville, Md., USA) were found to specifically bind the REK7-IgG. Furthermore, pretreatment of these cells with phosphatidylinositol-specific phospholipase C prior to incubation with REK7-IgG was found to decrease the binding of the REK7-IgG, suggesting the REK7 ligand is linked to the cell membrane by a glycophosphatidyl-inositol (GPI) anchor.

EXAMPLE 5

Purification of REK7 Ligand from BT20 Cells

BT20 cells were grown to 80% confluence in 150 mm plates, harvested by 5 mM EDTA in PBS, and seeded into 850 mm$^2$ roller bottles with growth medium. After 1 week of growth the cells were nearly confluent. The growth medium was removed, the cells washed with PBS, and serum-free growth medium was added. After 5 days, conditioned medium was harvested (12 liters from 72 roller bottles), centrifuged, sterile filtered, concentrated in a 12 kD molecular weight cutoff Amicon filter, and stored at −70° C.

200 ml of BT20 conditioned media, concentrated as described above from 12 liters and frozen, was thawed, centrifuged at 17,000 rpm in a Sorvall SS34 rotor, and filtered through a 0.45 µm filter to clarify the solution. The 200 ml was pumped through a 2.0 ml CD4-IgG—Protein A (CD4-IgG covalently linked to Protein A through IgG moiety) immunoaffinity precolumn and a 1.0 ml REK7-IgG—Protein A (REK7-IgG covalently linked to Protein A through IgG moiety) immunoaffinity column in tandem with a flow rate of 0.5 ml/min. All chromatography was carried out at 4° C. Following one complete passage of the media through both columns, the flow rate was reduced to 0.2 ml/min, and the media was recycled through both columns. Following the loading of the REK7-IgG column, the two column were separated from each other, washed with 10 column volumes of PBS, and then eluted with four separate washes of 100 mM sodium citrate, pH 3.0 (2 ml each for the CD4-IgG column and 1 ml each for the REK7-IgG column). The first two washes were allowed to immediately flow through the column whereas the last two were incubated for 15 minutes before collection. The eluates were brought to pH 7.4 by the addition of 50 mM potassium phosphate, and an aliquot of each was analyzed by sodium dodecycl sulfate (SDS)—polyacrylamide gel electrophoresis (PAGE). Following silver staining of the gel, stained band of approximately 28,000, 27,000, and 25,000 Daltons was seen from the eluate from the last two washes, that were not seen in eluate obtained by similar treatment of the CD4-IgG precolumn.

EXAMPLE 6

Protein Sequencing

The 28,000, 27,000, and 25,000 Dalton protein bands that were observed on SDS-PAGE were transferred to a PVDF membrane (Millipore Corporation) by electroblotting, and then subjected to amino acid sequencing using a Applied Biosystems 473A or 470A sequencer. The N-terminus of each of the 28,000 and 25,000 Dalton proteins was blocked, but the N-terminus of the 27,000 Dalton protein gave the following sequence: DRYAVYW(N)SSNPRFQRGDYHID-VXINDY (SEQ. ID NO. 12).

Separate sequence analysis of the three protein bands after cyanogen bromide cleavage or digestion with Lys-C endopeptidase indicated that the 28,000, 27,000, and 25,000 Dalton proteins were related. In particular, the 27,000 Dalton and 25,000 Dalton proteins appeared to be proteolytic processed forms of the 28,000 Dalton protein. Sequence analysis of the 28,000 Dalton band after digestion with Lys-C endopeptidase resulted in two sequences, one of which was nearly identical to the N-terminal sequence of the 27,000 Dalton protein and also had three additional N-terminal residues, AVA. The following internal amino acid sequences were determined for cyanogen bromide and Lys-C fragments of the proteins:

```
MKTIGVHDRVFDVNDKVENXLEPA      (SEQ. ID. NO. 13)

VNFDGYSAXDHTSKGFKRXEXNR       (SEQ. ID. NO. 14)

FQLFTPFSLGXEXRXGREXFYISXAIP   (SEQ. ID. NO. 15)

KRWECNRP                      (SEQ. ID. NO. 16)
```

EXAMPLE 7

Isolation of REK7 Ligand cDNA

Based on the above protein sequences obtained for the REK7 ligand, two degenerate PCR primers were synthesized for use in isolating cDNA encoding the REK7 ligand:

```
                              (SEQ. ID. NO. 17)
5' - CCCTCGAGGTCGACGAYMGITAYGCIGTNTAYTGGAA (SEQ. ID. NO. 18)
5' - CCGCGGTGCGGCCGCTCTAGARTAICCRTCRAARTTNACCAT.
```

These degenerate primers were used to amplify the cDNAs of a BT20 cell cDNA library using standard PCR methods, and two resulting amplified cDNAs were subcloned and sequenced. These cDNAs, approximately 180 bp and 135 bp in size, encoded deduced amino acid sequences matching the above amino acid sequences determined for the REK7 ligand. The 180 bp fragment was used to screen a human fetal brain cDNA library (containing approximately 2×10⁶ clones) by hybridization under high stringency conditions. The nucleotide sequence determined from two independent positive cDNA clones is shown in FIG. 2 (SEQ ID NO: 3), along with the deduced amino acid sequence of the REK7 ligand, termed AL-1 (SEQ ID NO: 4).

EXAMPLE 8

Biological Activity

Cerebral cortex from postnatal day 2 (P2) Wistar rat pups was dissected in 4° C. Hanks balanced salt solution (HBSS, calcium and magnesium free) under sterile conditions. After initial trituration with a 10 ml pipette, cells were dissociated by two passages through an 18 gauge injection cannula attached to a 10 ml syringe. The cell suspension was strained through a 70 μm cell strainer (Falcon) and centrifuged at 800 g for 5 minutes. Pelleted cells were resuspended in 50/50 (v/v) DMEM/F12 with 10% fetal bovine serum, 15 mM HEPES pH7.4. The cell suspension was plated into 75 cm² tissue culture flasks, and placed into a 37° C., 5% $CO_2$ incubator. Cultures were grown to confluence (10–15 days) and the medium was changed every 3 days. Once cultures were confluent the flasks were shaken in a rotary shaker at 300 rpm at 37° C. for 24 hrs to obtain purified astrocytes. Media with the suspended cells and debris was replaced and cultures were incubated for another 24 hours. Purified astrocyte cultures were trypsinized (0.05% trypsin, 0.025 mM EDTA in Hanks) from the flasks and then replated into 60 mm tissue culture treated dishes (2 dishes per 75 cm² flask).

Cerebral cortex of embryonic day 16 (E16) rats was dissected in 4° C. HBSS under sterile conditions. Media was changed to 1 ml of Defined Neuronal Medium (DNM, Peterson et al., Dev. Brain Res. 48:187–195 (1989) and cortices were triturated by pipeting 15 times through a plastic disposable pipet blue. 9 ml of DNM then was added and the cell suspension was strained through a 45 μm cell strainer and centrifuged at 800 g for 5 minutes. Pelleted cells were resuspended in 5 ml of DNM and 4×10⁵ cells were plated onto 60 mm dishes containing astrocytes which had been pretreated for 6 hours with either REK7-IgG (30 μg/ml), CD4-IgG (30 μg/ml), or no added IgG (control). Cultures were grown for 4 days and then fixed for 15 minutes with 4% paraformaldehyde in 100 mM Sodium Phosphate buffer, pH 7.4, followed by 3 washes with PBS.

The addition of REK7-IgG to the co-cultures completely prevented the formation of axon bundles. In contrast, the addition of CD4-IgG, and other IgGs had no effect on axon bundling. These results indicate a role for REK7 and its ligand, AL-1, in axon fasciculation, which is a crucial step in the development of the nervous system during regeneration following injury.

Consistent with that role, we also found that upon incubation of the cultured neuronal cells with labelled anti-REK7 antibodies, there was specific binding of the antibodies to the surface of axonal fibers within axon bundles. Furthermore, when cells expressing REK7 were incubated with AL-1, specific phosphorylation of REK7 was observed, indicating that AL-1 not only binds to REK7 but also activates REK7.

What is claimed is:

1. A method of promoting the growth and/or survival of motor neurons, comprising treating said neurons with an effective amount of a polypeptide comprising amino acid residues 21 to 228 of the AL-1 amino acid sequence of SEQ ID NO: 4.

2. The method of claim 1, wherein the polypeptide is a fusion of amino acid residues 21 to 228 of the AL-1 amino acid sequence of SEQ ID NO: 4 and an immunoglobulin domain.

3. The method of claim 2, wherein the immunoglobulin domain is an immunoglobulin constant region.

4. The method of claim 1 that further comprises administering a therapeutically effective amount of Nerve Growth Factor, Brain Derived Neurotrophic Factor, Neurotrophin-3 or Neurotrophin-4/5.

* * * * *